United States Patent
Tidmarsh et al.

(10) Patent No.: US 8,067,451 B2
(45) Date of Patent: *Nov. 29, 2011

(54) METHODS AND MEDICAMENTS FOR ADMINISTRATION OF IBUPROFEN

(75) Inventors: George Tidmarsh, Portola Valley, CA (US); Barry L. Golombik, Incline Village, NV (US); Puneet Sharma, Gaithersburg, MD (US)

(73) Assignee: Horizon Pharma USA, Inc., Northbrook, IL (US)

( * ) Notice: Subject to any disclaimer, the term of this patent is extended or adjusted under 35 U.S.C. 154(b) by 932 days.

This patent is subject to a terminal disclaimer.

(21) Appl. No.: 11/779,204

(22) Filed: Jul. 17, 2007

(65) Prior Publication Data

US 2008/0063706 A1    Mar. 13, 2008

Related U.S. Application Data

(63) Continuation-in-part of application No. 11/489,705, filed on Jul. 18, 2006, and a continuation-in-part of application No. 11/489,272, filed on Jul. 18, 2006, and a continuation-in-part of application No. 11/489,269, filed on Jul. 18, 2006, and a continuation-in-part of application No. 11/489,275, filed on Jul. 18, 2006.

(60) Provisional application No. 60/897,371, filed on Jan. 24, 2007.

(51) Int. Cl.
  *A61K 31/19* (2006.01)
  *A61K 31/425* (2006.01)
  *A61K 9/20* (2006.01)
(52) U.S. Cl. .................. 514/370; 514/570; 424/464
(58) Field of Classification Search .................. 514/370, 514/569, 570
  See application file for complete search history.

(56) References Cited

U.S. PATENT DOCUMENTS

| | | | |
|---|---|---|---|
| 4,283,408 A | 8/1981 | Hirata et al. | |
| 4,757,060 A | 7/1988 | Lukacsko et al. | |
| 5,037,815 A | 8/1991 | Lukacsko et al. | |
| 5,120,850 A | 6/1992 | Bod et al. | |
| 5,128,477 A | 7/1992 | Bod et al. | |
| 5,204,118 A | 4/1993 | Goldman | |
| 5,364,616 A | 11/1994 | Singer et al. | |
| 5,384,130 A | 1/1995 | Kamada et al. | |
| 5,417,980 A | 5/1995 | Goldman et al. | |
| 5,466,436 A | 11/1995 | Stables | |
| 5,496,836 A | 3/1996 | De Rocco et al. | |
| 5,505,983 A | 4/1996 | Kamada | |
| 5,601,843 A | 2/1997 | Gimet et al. | |
| 5,696,165 A | 12/1997 | Armitage et al. | |
| 5,747,068 A | 5/1998 | Mendizabal | |
| 5,854,267 A | 12/1998 | Berlin et al. | |
| 5,976,578 A | 11/1999 | Beyerle | |
| 6,149,943 A | 11/2000 | McTeigue et al. | |
| 6,294,192 B1 | 9/2001 | Patel et al. | |
| 6,455,518 B2 | 9/2002 | Zenke et al. | |
| 6,544,556 B1 | 4/2003 | Chen et al. | |
| 6,552,047 B2 | 4/2003 | Garvey et al. | |
| 6,569,463 B2 | 5/2003 | Patel et al. | |
| 6,613,354 B2 | 9/2003 | Depui et al. | |
| 6,660,303 B2 | 12/2003 | Staniforth | |
| 6,923,988 B2 | 8/2005 | Patel et al. | |
| 6,926,907 B2 | 8/2005 | Plachetka | |
| 6,951,657 B1 * | 10/2005 | Zuccarelli et al. | 424/497 |
| 2003/0069255 A1 | 4/2003 | Plachetka | |
| 2003/0178031 A1 | 9/2003 | Du Pen et al. | |
| 2004/0235802 A1 | 11/2004 | Gimona et al. | |
| 2005/0020671 A1 | 1/2005 | Ibanez et al. | |
| 2005/0053655 A1 | 3/2005 | Yang et al. | |
| 2005/0163847 A1 | 7/2005 | Cheng et al. | |
| 2005/0196459 A1 * | 9/2005 | Castan et al. | 424/490 |
| 2005/0249806 A1 * | 11/2005 | Proehl et al. | 424/464 |
| 2005/0249811 A1 | 11/2005 | Plachetka | |
| 2006/0127478 A1 | 6/2006 | Zerbe et al. | |
| 2006/0177504 A1 | 8/2006 | Sundharadas | |
| 2007/0003490 A1 | 1/2007 | Nijhawan | |
| 2007/0043096 A1 | 2/2007 | Tidmarsh et al. | |
| 2007/0043097 A1 | 2/2007 | Tidmarsh et al. | |
| 2008/0020040 A1 | 1/2008 | Tidmarsh et al. | |
| 2008/0021078 A1 | 1/2008 | Tidmarsh et al. | |
| 2008/0063706 A1 | 3/2008 | Tidmarsh et al. | |
| 2010/0297224 A1 | 11/2010 | Tidmarsh et al. | |

FOREIGN PATENT DOCUMENTS

| | | |
|---|---|---|
| EP | 0 321 613 A1 | 6/1989 |
| EP | 0320550 A1 | 6/1989 |
| GB | 2 105 193 A | 9/1982 |
| GB | 2 105 193 A | 3/1983 |
| WO | WO-91/16886 | 11/1991 |
| WO | WO 94/07541 | 4/1994 |
| WO | WO 02/22108 A1 | 3/2002 |
| WO | WO 02/066002 A2 | 8/2002 |
| WO | WO-02/098352 | 12/2002 |
| WO | WO 2004/064815 A1 | 8/2004 |

(Continued)

OTHER PUBLICATIONS

Brady, W. M., M.D. et al., "Gastroesophageal reflux disease the long and the Short of therapeutic options," *Postgraduate Medicine online*, 100(5) (1996).
Chremos, A. N., M.D., "Clinical Pharmacology of Famotidine: A Summary," *J Clin Gastroenterol*, 9(Suppl. 2): 7-12 (1987).
Chremos, A. N., M.D., "Pharmacodynamics of Famotidine in Humans," *Am J Med*, 81(suppl 4B): 24 (1986).
Edge, D.P., "High dose famotidine in ranitidine resistant severe oesophagitis: a pilot study," *New Zealand Medical Journal*, 11:150-152 (1990).
Porro, G. B., "Famotidine in the Treatment of Gastric and Duodenal Ulceration: Overview of Clinical Experience," *Karger (Intl J Gastroenterology) Digestion*, 32(suppl. 1): 62-69 (1985).

(Continued)

*Primary Examiner* — Jennifer M Kim
(74) *Attorney, Agent, or Firm* — Foley & Lardner LLP

(57) ABSTRACT

A method for administration of ibuprofen to a subject in need of ibuprofen treatment is provided, in which an oral dosage form comprising a therapeutically effective amount of ibuprofen and a therapeutically effective amount of famotidine is administered three times per day.

10 Claims, 2 Drawing Sheets

FOREIGN PATENT DOCUMENTS

Figure 1A:
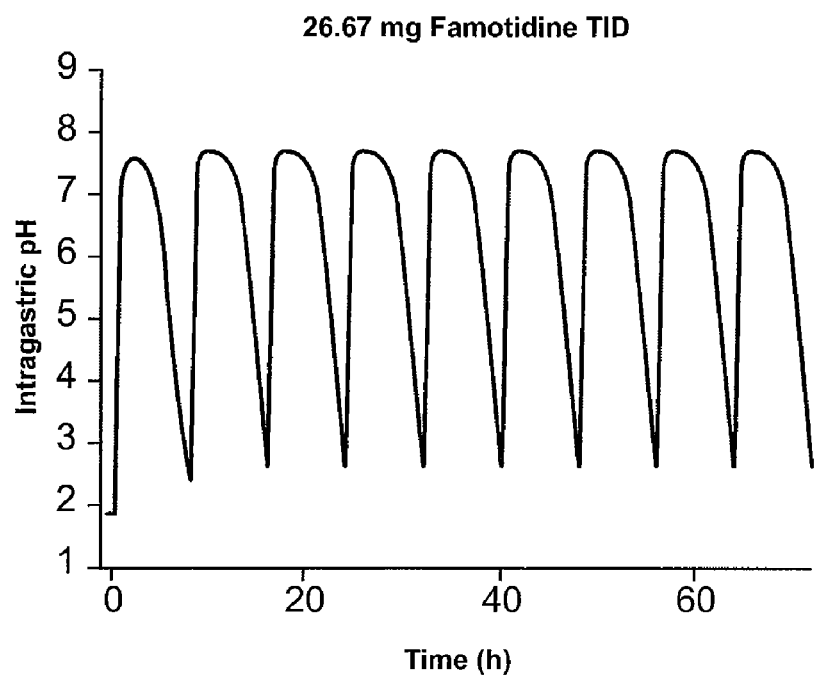

| WO | WO 2007/012019 | 1/2007 |
|----|----------------|--------|
| WO | WO-2007/012022 | 1/2007 |
| WO | WO 2008/011426 A2 | 1/2008 |
| WO | WO-2008/027963 | 3/2008 |
| WO | WO-2010/009432 | 1/2010 |

OTHER PUBLICATIONS

Santana, et al., "Effect of oral famotidine on 24-hour intragastric acidity," *Postgraduate Medical Journal* (UK) 62(Suppl 2):39-42 (1986).

Smith, J. L., "Clinical Pharmacology of Famotidine," *Karger (Intl J Gastroenterology) Digestion*, 32(suppl. 1):15-23 (1985).

Taha, A. et al., "Famotidine for the Prevention of Gastric and Duodenal Ulcers caused by Nonsteroidal Antiinflammatoty Drugs," *N. Engl. J. Med.*, 334:1435-1439 (1996).

Vinayek, R. et al., "Famotidine in the Therapy of gastric Hypersecretory States," *The American Journal of Medicine*, 81(S4B):49-59 (1986).

Abraham et al., "National adherence to evidence-based guidelines for the prescription of nonsteroidal anti-inflammatory drugs," Gastroenterology 129:1171-1178 (2005).

Altman "Review of Ibuprofen for Osteoarthritis," Am. J. Med. 10:18 (1984).

Aly et al., "Formulation and evaluation of famotidine and ibuprofen chewable tablets," Jordan Journal of Applied Sciences-Natural Sciences 6(2):1-7 (2004).

American College of Rheumatology Ad Hoc Group on Use of Selective and Nonselective Nonsteroidal Antiinflammatory Drugs "Recommendations for Use of Selective and Nonselective Nonsteroidal Antiinflammatory Drugs," Arthritis & Rheumatism 59(3):1058-1073 (2008).

American Hospital Formulary Service. Drug Information 88, p. 1659-1664 (1988).

American Society of Health-System Pharmacists, AHFS Drug Information 2006. McEvoy, ed., pp. 2902-2908 (2006).

Bell et al., "Time to maximum effect of lansoprazole on gastric pH in normal male volunteers," Aliment. Pharmacal. Ther. 10(6):897-904 (1996).

Chambers et al., "A Cohort Study of NSAID Use and the Management of Related Gastrointestinal Symptoms by Primary Care Patients" P&T 27(7):462-467 (Jul. 2003).

Copending U.S. Appl. No. 11/489,269, filed Jul. 18, 2006.

Copending U.S. Appl. No. 11/489,275, filed Jul. 18, 2006.

Copending U.S. Appl. No. 11/489,705, filed Jul. 18, 2006.

Davies "Clinical pharmacokinetics of ibuprofen. The first 30 years" Clin. Pharmacokinet. 34:101-154 (1998).

Davies, et al, Ibuprofen: a review of its pharmacological properties, Drugs, (1971), 2:416-446.

De Klerk et al., Abstract of "Patient compliance in rheumatoid arthritis polymyalgia rheumatic, and gout" J. Rheumatol. 30(1):44-54 (Jan. 2003).

Dial et al., "Proton pump inhibitor use and risk of community-acquired Clostridium difficile—associated disease defined by prescription for oral vancomycin therapy," CMAJ 175(7):745-748 (Sep. 26, 2006).

Doherty et al., "Multiple Endocrine Neoplasias" Cancer: Principles and Practice of Oncology, 6th edition. J.B. Lippincott Co. pp. 1834-1839 (2001).

Drug Facts and Comparisions, 1997 Edition pp. 1387-1399, pp. 1933-1947.

Echizen et al., "Clinical Pharmacokinetics of Famotidine," Clin. Pharmacokinet. 21(3):178-194 (1991).

European Supplementary Search Report and Search Opinion issued in Patent Application 06800140.3; Mail Date: Nov. 13, 2009, Completion Date: Nov. 2, 2009.

European Supplementary Search Report and Search Opinion issued in Patent Application 07813027.5; Mail Date: Oct. 27, 2009, Completion Date: Oct. 15, 2009.

FDA Facsimile dated May 16, 2006 regarding IND 72,116 HZT-501 (Ibuprofen and Famotidine) EOP2 Meeting.

Gabriel et al., "Risk for serious gastrointestinal complications related to use of nonsteroidal anti-inflammatory drugs. A meta-analysis," Ann. Intern. Med. 115(10):787-796 (1991).

Geis et al., "Prevalence of Mucosal Lesions in the Stomach and Duodenum Due to Chronic Use of NSAID in Patients with Rheumatoid Arthritis or Osteoarthritis, and Interim Report on Prevention by Misoprostol of Diclofenac Associated Lesions," J. Rheumatol. 18(suppl 28):11-14 (1991).

Gillin et al., "Problems related to acid rebound and tachyphylaxis" Best Practice & Research Clinical Gastroenterology 15(3):487-495 (2001).

Ho et al., "Risk of Adverse Outcomes Associated with concomitant use of clopidogrel and proton pump inhibitors follong acute coronary syndrome" JAMA 301(9):937-944 (Mar. 4, 2009).

Horizon Therapeutics "Horizon Therapeutics" PowerPoint Presentation, May 12, 2009.

Horizon Therapeutics: "PIND 72,116 / ibuprofen/famotidine combo product Pre-IND Meeting," (Jun. 13, 2005).

Howden et al., "The Tolerability and Safety of Famotidine" Clinical Therapeutics 18(1):36-54 (1996).

Hudson et al., "Famotidine for Healing and Maintenance in Nonsteroidal anti-inflammatory Drug-Associated Gastroduodenal Ulceration," Gastroenterology 112:1817-1822 (1997).

HZT-501 Follow-on Safety Study (HZ-CA-304), (2009).

HZT-501 Phase 3 Trials: Reduce-1 and Reduce-2, 2009.

Inpharma (1994) Symposia: Minimising the GI risks of NSAIDs. ISSN 1173-8324.

Investigator's Brochure, Horizon Therapeutics, (Feb. 28, 2007).

Kantor T.G., "Ibuprofen" Ann. of Int. Med. 91:1877-1882 (1979).

Koch et al., "Prevention of Nonsteroidal Anti-inflammatory Drug-Induced Gastrointestinal Mucosal Injury," Arch. Intern. Med. 156:2321-2332 (1996).

Krishna et al., "Newer H2-Receptor Antagonists: Clinical Pharmacokinetics and Drug Interaction Potential" Clinical Pharmacokinetics 15:205-215 (1988).

Lanza et al., "Guidelines for Prevention of NSAID-Related Ulcer Complications" Am. J. Gastroenterol. 104:728-738 (2009).

Larkai et al., "Dyspepsia in NSAID users: the size of the problem" J. Clin. Gastroenterol. 11(2):158-162 (1989).

Lin "Pharmacokinetic and pharmacodynamic properties of histamine H2-receptor antagonists. Relationship between intrinsic potency and effective plasma concentrations" Clin. Pharmacokinet. 20:218-236 (1991).

Loren et al., "Physicians Fail to Provide Protective Co-Therapy for High GI Risk Patients Taking NSAIDs-Even with Direct Interactive Communication and Free PPI: Results of a Prospective Outcomes Trial," Abstract DDW 2008.

Merki et al., "Double blind comparison of the effects of cimetidine, ranitidine, famotidine, and placebo on intragastric acidity in 30 normal volunteers" Gut 29:81-84 (1988).

Nwokolo et al., "Tolerance during 29 days of conventional dosing with cimetidine, nizatidine, famotidine or ranitidine" Aliment. Pharmacal. Ther. 4(suppl. 1):29-45 (1990).

PDR 53rd Edition, pp. 1856-1859 (1999).

Pelletier et al., "Efficacy & Safety of Diacerein in Osteoarthritis of the Knee" Arthritis & Rheumatism 43(10):2339-2348 (2000).

PEPCID (famotidine) tablet, film coated [Merck & Co., Inc.], retrieved Mar. 14, 2009 from http://dailymed.nlm.nih.gov/dailymed/drugInfo.cfm?id=8919.

Pifferi et al., "Quality and functionality of excipients" Farmaco 54(1-2):1-14 (2005).

Plachetka et al., "Integrated Gastric Acidity Can Predict the Prevention of Naproxen-Induced Gastroduodenal Pathology in Normal Subjects," American Gastroenterological Association Meeting (2003).

Pre-IND Meeting Background Information: "Fixed Dose Combination Product of ibuprofen and famotidine for Pain Relief," May 9, 2005.

Protocol: "Double Blind Follow on Safety Study of HZT-501 in Subjects Who Have Completed Participation in Horizon Protocol HZ-CA-301 or Horizon Protocol HZ-CA-303," Feb. 28, 2007.

U.S. Appl. No. 60/700,481, filed Jul. 18, 2005.

Rammer et al., "Prophylaxe NSAR-induzierter Ulzera" Journal für Gastroenterologische und Hepatologische Erkrankungen [online] 2(4) (2004). Retrieved from the Internet: http://www.kup.at/kup/pdf/4820.pdf [retrieved on Oct. 30, 2009].

Richy et al. "Time dependent risk of gastrointestinal complications induced by non-steroidal anti-inflammatory drug use: a consensus statement using a meta-analytic approach" Ann. Rheum. Dis. 63:759-766 (2004).

Rodriguez et al., "Risk of upper gastrointestinal bleeding and perforation associated with individual non-steroidal anti-inflammatory drugs" Lancet 343(8900):769-72 (1994).

Rostom et al., "Prevention of NSAID-induced gastrointestinal ulcers" Cochrane Database Syst. Rev. 4:CD002296 (2002).

Roumie et al., "Nonaspirin NSAIDs, Cyclooxygenase 2 Inhibitors, and the Risk for Stroke," Stroke (39):2037-2045 (2008).

Scheiman "Nonsteroidal Anti-Inflammatory Drugs, Aspirin, and Gastrointestinal Prophylaxis: An Ounce of Prevention" Reviews in Gastroenterological Disorders 5(2):S39-S49 (2005).

Schnitzer et al., "Use of nonsteroidal anti-inflammatory drugs and gastroprotective agents before the advent of cyclooxygenase-2-selective inhibitors: analysis of a large United States claims database." Clinical Therapeutics 2001 vol. 23 No. 12 1984-1998.

ScienceDaily, "Proton Pump Inhibitors Increase Risk of Heart Attacks for Patients on Common Cardiac Drug, Study Shows," Jan. 30, 2009.

Silverstein et al., "Misoprostol reduces serious gastrointestinal complications in patients with rheumatoid arthritis receiving anti-inflammatory drugs. A randomized, double-blind, placebo-controlled trial" Ann. Intern. Med. 123(4):241-249 (1995).

Simon et al., "A Dose-Ranging Study of Famotidine in Prevention of Gastroduodenal Lesions Associated with Nonsteroidal Anti-inflammatory Drugs (NSAIDS): Results of a U.S. Multicenter Trial" Abstracts Submitted for 59th Annual Scientific Meeting American College of Gastroenterology. Am. J. Gastroenterol. 89(9):1644 (1994).

Singh et al., "Gastrointestinal tract complications of nonsteroidal anti-inflammatory drug treatment in rheumatoid arthritis. A prospective observational cohort study" Arch. Intern. Med. 156(14):1530-1536 (1996).

Singh et al., "NSAID Induced Gastrointestinal Complications: The ARAMIS Perspective—1997" J. Rheumatol. 25(suppl 51):8-16 (1998).

Singh et al., "Decreased Use of Cox-2 Inhibitors is Increasing Gastrointestinal Complications," American College of Rheumatology (ACR), (Oct. 30, 2007).

Singh, G. "Recent Considerations in Non-Steroidal Anti-Inflammatory Gastropathy" Am. J. Med. 105(18):31S-38S (1998).

Smalley et al., "Nonsteroidal Anti-inflammatory Drugs and the Incidence of Hospitalizations for Peptic Ulcer Disease in Elderly Persons" Am. J. Epidemiology 141(6):539-545 (1995).

Sørensen et al. "Risk of upper gastrointestinal bleeding associated with use of low-dose aspirin" Am. J. Gastroenterol. 995(9):2218-2224 (2000).

Sturkenboom et al., "Adherence-to-proton pump inhibitors or H2-receptor antagonists during the use of non-steroidal anti-inflammatory drugs" Aliment Pharmacol. Ther., 18(11-12):1137-1147 (2003).

Suzuki et al. "Four-day continuous gastric pH monitoring following anti-acid secretory drug administration: cross-over test to assess the early effects" Aliment Pharmacol. Ther., 27(1):66-71 (2007).

Swift et al., "Effect of Ranitidine on Gastroduodenal Mucosal Damage in Patients on Long Term Non Steroidal Anti-inflammatory Drugs," Digestion 44:86-94 (1989).

Tamura et al. "Effects of Diacerein on Indomethacin-Induced Gastric Ulceration" Pharmacology 63:228-233 (2001).

Targownik et al., "Use of proton pump inhibitors and risk of osteoporosis-related fractures," CMAJ, 179(4):319-326 (Aug. 12, 2008).

Thiefin et al., "Characteristics and Impact of Upper GI Symptoms in Patients Treated with NSAIDs: Results of a Cross Sectional Epidemiological Study in Primary Care," Abstract DDW Presentation, (May 2008).

U.S. Appl. No. 11/489,272—Non-final Office Action (Restriction Requirement) dated Dec. 16, 2009.

U.S. Appl. No. 11/489,272—Non-final Office Action dated Oct. 14, 2010.

U.S. Appl. No. 11/489,275—Non-final Office Action (Restriction Requirement) dated Dec. 31, 2009.

U.S. Appl. No. 11/489,275—Non-final Office Action (Restriction Requirement) dated Sep. 10, 2010.

U.S. Appl. No. 11/489,705—Non-final Office Action (Restriction Requirement) dated Dec. 31, 2009.

U.S. Appl. No. 11/489,705—Non-final Office Action dated Oct. 1, 2010.

U.S. Appl. No. 11/489,269, filed Jul. 18, 2006: Prosecution History through Jun. 15, 2010.

Valenti, "Expanding role of coformulations in the treatment of HIV infection: impact of fixed dose combinations," Antiretroviral Therapy (Dec. 21, 2004).

Ward, "Update on Ibuprofen for Rheumatoid Arthritis," Am. J. Med. 77(1A): 39 (1984).

Wolfe et al., "Gastrointestinal Toxicity of Nonsteroidal Antiinflammatory Drugs," N.E. J. Med. 340(24):1888-1899 (1999).

Wu et al., "Does famotidine have similar efficacy to misoprostol in the treatment of non-steroidal anti-inflammatory drug-induced gastropathy?" IJCP 52(7):472-474 (Oct. 1998).

Yang et al., "Long term proton pump inhibitor therapy and risk of hip fracture," JAMA, vol. 296 No. 24:2947-2953 (Dec. 27, 2006).

Yazdanian et al., "The 'High Solubility' Definition of the Current FDA Guideline on Biopharmaceutical Classification System May Be Too Strict for Acidic Drugs," Pharmaceutical Res. 21(2):293-299 (2004).

Zeleznik et al., "High Functionality Excipients (HFE)—PROSOL® SMCC as an Effective Strategy for Generic Drug Formulation," Business Briefing: Pharmagenerics (2004).

Federal Register, vol. 75, No. 169, Wednesday, Sep. 1, 2010.

Opadrye® II Brochure, 1990.

FDA Drug Bulletin, vol. 19, No. 1, Feb. 1989.

Copending U.S. Appl. No. 11/489,272, filed Jul. 18, 2006; Inventors: George Tidmarsh, et al.

International Search Report and Written Opinion for PCT/US06/028075 dated Aug. 3, 2007.

Brady, W. M., M.D. et al., "Gastroesophageal reflux disease The long and the Short of therapeutic options," *Postgraduate Medicine online*, 100(5) (1996).

Castell, D.O., "Rationale for high-dose $H_2$-receptor blockade in the treatment of gastro-oesophageal reflux disease," *Aliment. Pharmacol. Therap.*, 1991, 5 (Suppl. 1), 59-67.

Cohen, "Dose Discrepancies Between the Physicians Desk Reference and the Medical Literature, and Their Possible Role in the High Incidence of Dose-Related Adverse Drug Events", *Archive of Internal Medicine*, Apr. 9, 2001, 161: 957-964.

DRUGS.COM, Famotidine Tablets, www.drugs.com/pro/famotindine, downloaded Jun. 7, 2007.

EMBASE Abstract of Adel et al., 2004, "Formulation and evaluation of famotidine and ibuprofen chewable tablets," Jordan Journal of Applied Sciences—Natural Sciences, vol. 6, No. 2, pp. 1-7.

Johnson, D., "Medical Therapy for Gastroesophageal Reflux Disease," *Amer. J. Med.*, May 27, 1992, vol. 92 (suppl. 5A), pp. 5A-88S-5A-97S.

Welage, "Overview of pharmacologic agents for acid suppression in critically ill patients", *American Journal of Health-System Pharmacy*, May 15, 2005, vol. 62, No. 10, Suppl. 2, pp. S4-S11.

Analysis of HZ-CA-004 Study Data, prepared Nov. 2007.

International Search Report and Written Opinion for PCT/US07/73716 dated Sep. 24, 2008.

U.S. Appl. No. 11/489,275—Non-final Office Action dated Jan. 19, 2011.

* cited by examiner

METHODS AND MEDICAMENTS FOR ADMINISTRATION OF IBUPROFEN

1.0 CROSS-REFERENCE TO RELATED APPLICATIONS

This application is a continuation-in-part of U.S. patent application Ser. No. 11/489,705; a continuation-in-part of U.S. patent application Ser. No. 11/489,272; a continuation-in-part of U.S. patent application Ser. No. 11/489,269 and a continuation-in-part of U.S. patent application Ser. No. 11/489,275 (all filed Jul. 18, 2006), and claims benefit under 35 USC §119(e) to U.S. provisional application No. 60/897,371 (filed Jan. 24, 2007). The entire contents of each of these applications is herein incorporated by reference for all purposes.

2.0 FIELD OF THE INVENTION

The invention relates to pharmaceutical compositions containing ibuprofen and famotidine, and finds application in the field of medicine.

3.0 BACKGROUND OF THE INVENTION

Ibuprofen, a non-steroidal anti-inflammatory drug (NSAID), has been used in humans for nearly forty years. While generally regarded as safe, ibuprofen and other NSAIDs can cause gastritis, dyspepsia, and gastric and duodenal ulceration. Gastric and duodenal ulceration is a consequence of impaired mucosal integrity resulting from ibuprofen-mediated inhibition of prostaglandin synthesis. This side-effect is a particular problem for individuals who take ibuprofen for extended periods of time, such as patients suffering from rheumatoid arthritis and osteoarthritis.

The risk of developing gastric or duodenal ulceration can be reduced by cotherapy with the drug famotidine. Famotidine blocks the action of the histamine type 2 (H2) receptor, leading to a reduction of acid secretion in the stomach. Reducing stomach acid with famotidine during treatment with certain nonsteroidal anti-inflammatory drugs is reported to decrease incidence of gastrointestinal ulcers (see Taha et al., 1996, "Famotidine for the prevention of gastric and duodenal ulcers caused by nonsteroidal anti-inflammatory drugs" *N Engl J Med* 334:1435-9, and Rostom et al., 2002, "Prevention of NSAID-induced gastrointestinal ulcers" *Cochrane Database Syst Rev* 4:CD002296).

Famotidine is used for treatment of heartburn, ulcers, and esophagitis at daily doses from 10 mg to 80 mg. Approved schedules of famotidine administration include 10 or 20 mg QD or BID (for treatment of heartburn), 20 mg or 40 mg QD (for healing ulcers, such as 40 mg HS for 4-8 weeks for healing duodenal ulcers), 20 mg HS (maintenance dose following healing of ulcer), 20 mg BID for 6 weeks (for treatment of gastroesophageal reflux disease), and 20 or 40 mg BID (for treatment of esophageal erosion). For treatment of Zollinger-Ellison Syndrome, a disease characterized by hypersecretion of gastric acid, doses of up to 800 mg/day have been used.

Although NSAID plus famotidine cotherapy reduces risk of developing gastric or duodenal ulceration, present therapies are not widely used. More effective methods of treatment and pharmaceutical compositions are needed. The present invention meets this and other needs.

4.0 BRIEF SUMMARY OF THE INVENTION

In one aspect the invention provides a method for reducing gastric acid while treating a patient with an ibuprofen-responsive condition. The method involves administering a first dose of an oral dosage form containing from 775 mg to 825 mg ibuprofen and from 25 mg to 28 mg famotidine, where the ibuprofen and famotidine are present in a weight ratio in the range 29:1 to 31:1, and where the ibuprofen and the famotidine are formulated for immediate release; administering a second dose of the oral dosage form; and administering a third dose of the oral dosage form, where the first dose, the second dose, and the third dose are administered within a 24 hour dosing cycle. In one embodiment, the ibuprofen and the famotidine are admixed in the oral dosage form. In one embodiment, the ibuprofen and the famotidine are in separate compartments in the oral dosage form.

The ibuprofen and the famotidine may be formulated to release at least 60% of the ibuprofen and the famotidine within about 20 minutes under neutral pH conditions.

In one aspect the invention provides an oral dosage form comprising from 775 mg to 825 mg ibuprofen and from 25 mg to 28 mg famotidine, the ibuprofen and famotidine being present in a weight ratio in the range 29:1 to 31:1, where the ibuprofen and the famotidine are formulated for immediate release. In one embodiment the oral dosage form comprises a first portion containing ibuprofen and a second portion containing famotidine, where the famotidine is in the form of barrier-coated particles distributed in the ibuprofen portion.

In one aspect the invention provides a method of reducing the likelihood that a patient receiving combined ibuprofen-famotidine therapy will experience a 24-hour median pH less than 2.5, by administering a oral unit dosage form to the patient on a TID (three-times-per-day) schedule.

In one aspect the invention provides a method for reducing patient-to-patient variability with respect to gastric pH in a population of patients in need of an ibuprofen-famotidine combination therapy by administering to patients in the population an oral unit dosage form containing ibuprofen and famotidine, where the ibuprofen and famotidine are in a weight ratio in the range of 29:1 to 31:1, and the oral unit dose form is administered three-times-per-day (TID). In one embodiment the oral unit dosage form contains about 800 mg ibuprofen and about 26.67 mg famotidine or about 400 mg ibuprofen and about 13.33 mg famotidine.

In one aspect the invention provides an improved method for treating a population of patients in need of an ibuprofen-famotidine combination therapy and reducing inter-patient variability with respect to gastric pH in the population. The method involves administering to patients in the population an oral unit dosage form containing ibuprofen and famotidine, where the ibuprofen and famotidine are in a weight ratio in the range of 29:1 to 31:1, and the oral unit dose form is administered three-times-per-day.

In one aspect, the invention provides a method for administration of ibuprofen to a subject in need of ibuprofen treatment. The method involves administering an oral dosage form containing a therapeutically effective amount of ibuprofen and a therapeutically effective amount of famotidine, where the oral dosage form is administered three times per day (TID). In one embodiment, the ibuprofen and the famotidine are in separate compartments of the oral dosage form. In one embodiment, the ibuprofen and the famotidine are in admixture in the oral dosage form. In one embodiment, the famotidine and ibuprofen are released from the dosage form rapidly, e.g., under in vitro assay conditions.

In one embodiment, ibuprofen and famotidine are administered in daily doses of about 2400 mg and about 80 mg respectively. In some embodiments of this method, the oral dosage form contains ibuprofen and famotidine in a ratio in the range of 29:1 to 32:1, such as the range of 30:1 to 31:1. In one embodiment, the oral dosage form contains 750 mg to 850 mg (e.g. about 800 mg) ibuprofen and 24 mg to 28 mg (e.g., about 26.6 mg famotidine). In one embodiment, the oral dosage form contains 775 mg to 825 mg (e.g. about 800 mg) ibuprofen and 24 mg to 28 mg (e.g., about 26.6 mg famotidine). In another embodiment, the oral dosage form contains 375 mg to 425 mg (e.g., about 400 mg) ibuprofen and 12 mg to 14 mg (e.g., about 13 mg) famotidine.

In one embodiment, the TID administration of the dosage form provides better gastric protection for the subject over a 24-hour period than TID administration of the same daily quantity of ibuprofen and two times a day (BID) administration of the same daily quantity of famotidine. In one embodiment, the daily quantity of ibuprofen is about 2400 mg and the daily quantity of famotidine is about 80 mg. Thus, in certain aspects, the invention provides a method in which TID administration of a dosage form containing about 800 mg ibuprofen and about 26.6 mg famotidine provides better gastric protection over a 24-hour period than TID administration of the 800 mg ibuprofen and BID administration of 40 mg famotidine. Equivalently, TID administration of two oral dosage forms containing about 400 mg ibuprofen and about 13 mg (e.g., about 13.3 mg) famotidine provides better gastric protection over a 24-hour period than TID administration 800 mg ibuprofen in a single or split dose and BID administration of 40 mg famotidine in a single or split dose.

Ibuprofen, in the form of a unit dose form of the invention, may be administered to a subject is in need of ibuprofen treatment. In various embodiments, the subject is in need of ibuprofen treatment for a chronic condition (such as rheumatoid arthritis, osteoarthritis or chronic pain) or a condition such as acute or moderate pain, dysmenorrhea or acute inflammation.

In a different aspect the invention provides a solid oral dosage form having a first portion containing a therapeutically effective amount of ibuprofen and a second portion containing a therapeutically effective amount of famotidine, where the first portion completely surrounds the second portion or the second portion completely surrounds the first portion; and having a barrier layer disposed between the first and second portions, where the ibuprofen and famotidine are released into solution rapidly. In one embodiment an ibuprofen-containing core portion is surrounded by a famotidine-containing layer and a barrier layer is interposed between the core portion and famotidine-containing layer.

In another aspect, a solid oral dosage form is provided which comprises particles of famotidine coated with a barrier layer and situated in a matrix containing ibuprofen or compressed into a tablet with ibuprofen and excipients. In one aspect, the ibuprofen is ibuprofen DC-85 from BASF.

In one embodiment, the oral dosage form contains about 800 mg ibuprofen and about 26.6 mg (e.g., 26.67 mg) famotidine or about 400 mg ibuprofen and about 13 mg (e.g., 13.3 mg) famotidine. In some embodiments, the oral dosage form contains ibuprofen and famotidine in a ratio in the range of 29:1 to 32:1. In some embodiments, the oral dosage form contains ibuprofen and famotidine in a ratio in the range of 29:1 to 31:1.

In a specific embodiment, first portion comprises ibuprofen, 20-30% (w/w) lactose monohydrate; 0.1 to 2% colloidal silicon dioxide; 3-7% crosscarmellose sodium; 1-3% hydroxy propyl methyl cellulose; 2-6% silicified microcrystalline cellulose (Prosolv SMCC 90) and 0.1-2% magnesium stearate.

In one embodiment, at least 75% of the famotidine and at least 75% of the ibuprofen in the dosage form are released within 15 minutes when measured in a Type II dissolution apparatus (paddles) according to U.S. Pharmacopoeia XXIX at 37° C. in 50 mM potassium phosphate buffer, pH 7.2 at 50 rotations per minute.

In an aspect of the invention a method is provided for treating a patient in need of ibuprofen treatment, where the patient is at elevated risk for developing an NSAID-induced ulcer. The method involves administering an oral dosage form comprising a therapeutically effective amount of ibuprofen and a therapeutically effective amount of famotidine, where the oral dosage form is administered three times per day (TID), where the ibuprofen and the famotidine are optionally in separate compartments of the oral dosage form, and where the famotidine and ibuprofen are released from the dosage form rapidly when agitated in 50 mM potassium phosphate buffer, pH 7.2 at 37° C. In one embodiment of this method the oral dosage form may contain ibuprofen and famotidine in a ratio in the range of 30:1 to 31:1.

In an aspect of the invention a method is provided for reducing symptoms of dyspepsia in a subject in need of NSAID treatment who has experienced symptoms of dyspepsia associated with NSAID administration, comprising administering to the subject an effective amount of a NSAID in combination with an effective amount of famotidine, where the famotidine is administered three times per day. In one embodiment of this method the NSAID is ibuprofen. In one embodiment of this method from 25 mg to 27 mg famotidine is administered three times per day. In one embodiment of this method the famotidine and NSAID are administered as a single oral unit dose form.

In an aspect of the invention a method is provided for treating a person in need of famotidine treatment by administering from 25 mg to 27 mg famotidine three times per day. In a related aspect, the invention provides a solid oral dosage form comprising famotidine or a pharmaceutically acceptable salt thereof, and one or more pharmaceutically acceptable excipients, where the dosage form comprises about 13 mg (e.g., 13.3 mg) or about 26.6 mg famotidine. In one embodiment famotidine is the only pharmaceutically active ingredient in the dosage form.

In an aspect of the invention a method is provided for administration of ibuprofen to a subject by providing an oral dosage form comprising 750 mg to 850 mg ibuprofen and 24 mg to 28 mg famotidine, where the ibuprofen and famotidine are present in a ratio in the range of 29:1 to 32:1; or in the range of 29:1 to 31:1, administering a first dose of the oral dosage form; administering a second dose of the oral dosage form; and administering a third dose of the oral dosage form, where the first dose, the second dose, and the third dose are administered within a 24 hour dosing cycle.

5.0 BRIEF DESCRIPTION OF THE FIGURES

Figure 1B:
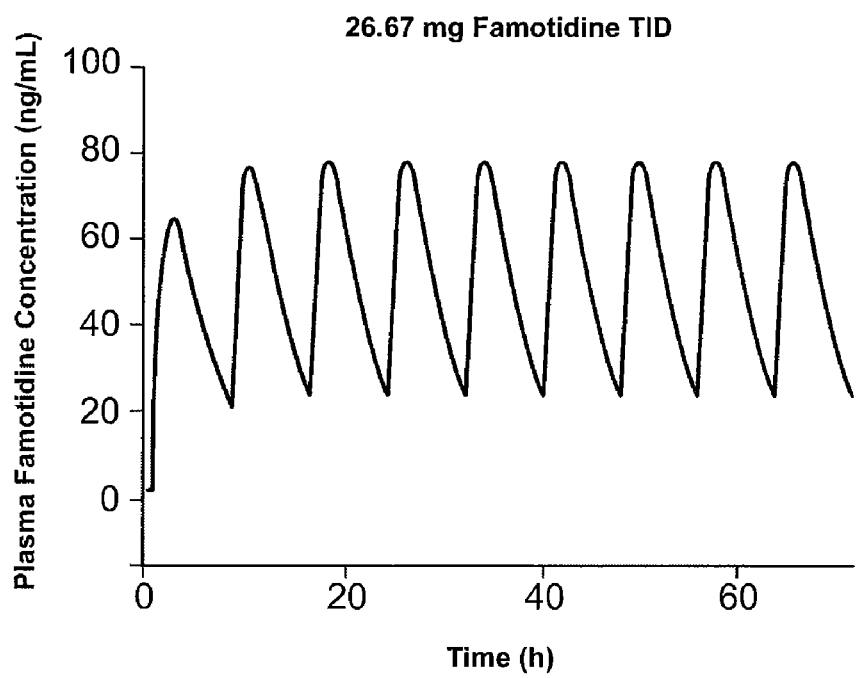

FIG. 1 shows the predicted effect on intragastric pH of administration of 26.6 mg famotidine TID. FIG. 1A (upper panel) shows the predicted intragastric pH during TID dosing of famotidine (80 mg/day). FIG. 1B (lower panel) shows the predicted plasma famotidine concentration during TID dosing of famotidine (80 mg/day).

Figure 2A:
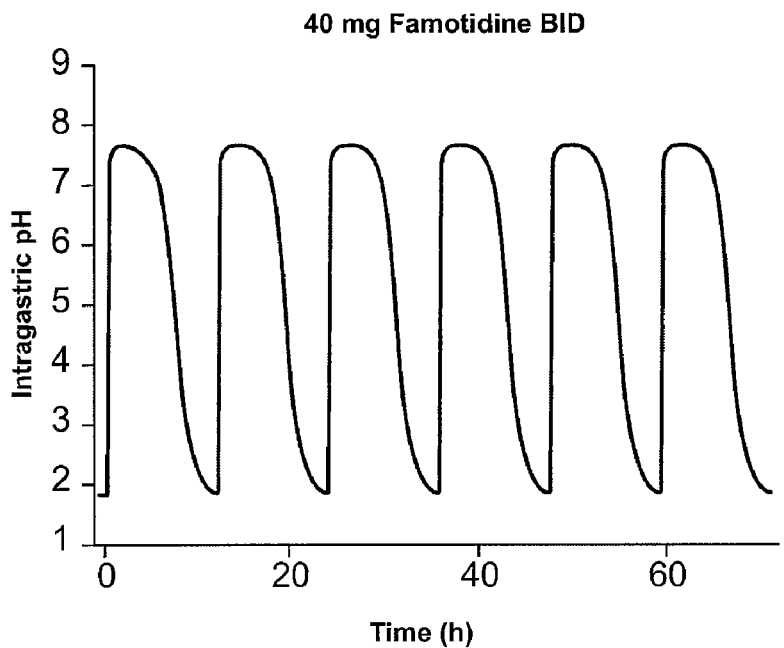
Figure 2B:
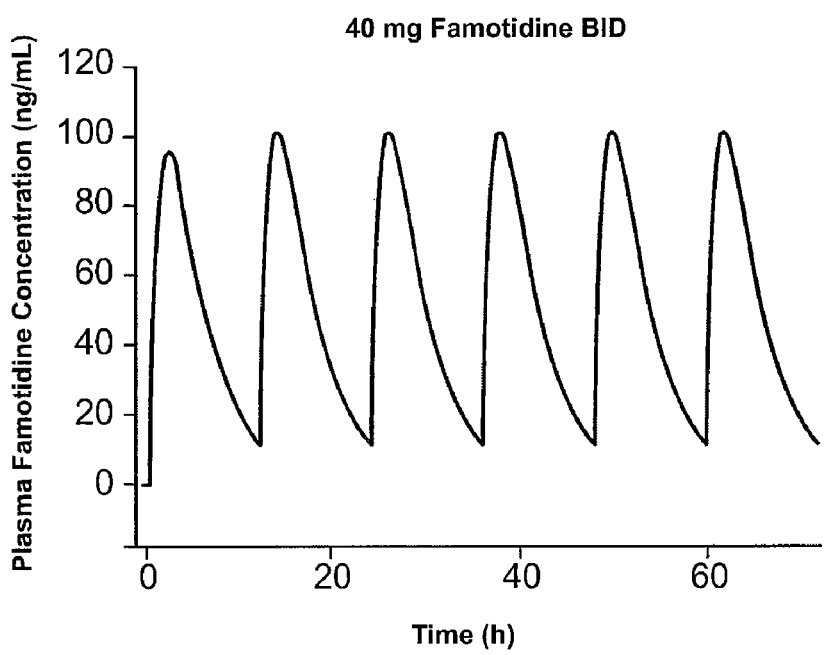

FIG. 2 shows the predicted effect on intragastric pH of administration of 40 mg famotidine BID. FIG. 2A (upper panel) shows the predicted intragastric pH during BID dosing of famotidine (80 mg/day). FIG. 2B (lower panel) shows the predicted plasma famotidine concentration during BID dosing of famotidine (80 mg/day).

6.0-18.10 DETAILED DESCRIPTION

6.0 Definitions

"Famotidine" is 3-[2-(diaminomethyleneamino)thiazol-4-ylmethylthio]-N-sulfamoyl propionamidine, including the polymorphic forms designated Form A and Form B (see, e.g. U.S. Pat. Nos. 5,128,477 and 5,120,850) and their mixtures, as well as pharmaceutically acceptable salts thereof. Famotidine can be prepared using art-known methods, such as the method described in U.S. Pat. No. 4,283,408. Famotidine's properties have been described in the medical literature (see, e.g., Echizen et al., 1991, *Clin Pharmacokinet.* 21:178-94).

"Ibuprofen" is 2-(p-isobutylphenyl) propionic acid ($C_{13}H_{18}O_2$), including various crystal forms and pharmaceutically acceptable salts. Two enantiomers of ibuprofen exist. As used herein in the context of solid formulations of the invention, "ibuprofen" refers to a racemic mixture or either enantiomer (including, for example, mixtures enriched in the S-enantiomer, and compositions substantially free of the R-enantiomer). Ibuprofen is available commercially and, for example, ibuprofen preparations with mean particle sizes of 25, 38, 50, or 90 microns can be obtained from BASF Aktiengesellschaft (Ludwigshafen, Germany). One useful ibuprofen product is directly compressible formulation described in WO 2007/042445 (incorporated herein by reference), a version of which is available from BASF under the trade name Ibuprofen DC 85™. Ibuprofen's properties have been described in the medical literature (see, e.g., Davies, 1998, "Clinical pharmacokinetics of ibuprofen. The first 30 years" *Clin Pharmacokinet* 34:101-54).

An "API" is an active pharmaceutical ingredient. As used herein, "API" refers to ibuprofen and/or famotidine.

A "therapeutically effective amount" of ibuprofen is an amount of ibuprofen or its pharmaceutically acceptable salt which eliminates, alleviates, or provides relief of the symptoms for which it is administered.

A "therapeutically effective amount" of famotidine is an amount of famotidine or its pharmaceutically acceptable salt which suppresses gastric acid secretion.

The terms "solid oral dosage form," "oral dosage form," "unit dose form," "dosage form for oral administration," and the like are used interchangably, and refer to a pharmaceutical composition in the form of a tablet, capsule, caplet, gelcap, geltab, pill and the like.

An "excipient," as used herein, is any component of an oral dosage form that is not an API. Excipients include binders, lubricants, diluents, disintegrants, coatings, barrier layer components, glidants, and other components. Excipients are known in the art (see HANDBOOK OF PHARMACEUTICAL EXCIPIENTS, FIFTH EDITION, 2005, edited by Rowe et al., McGraw Hill). Some excipients serve multiple functions or are so-called high functionality excipients. For example, talc may act as a lubricant, and an anti-adherent, and a glidant. See Pifferi et al., 2005, "Quality and functionality of excipients" *Farmaco.* 54:1-14; and Zeleznik and Renak, *Business Briefing: Pharmagenerics* 2004.

A "binder" is an excipient that imparts cohesive qualities to components of a pharmaceutical composition. Commonly used binders include, for example, starch; sugars, such as, sucrose, glucose, dextrose, and lactose; cellulose derivatives such as powdered cellulose, microcrystalline cellulose, silicified microcrystalline cellulose (SMCC), hydroxypropylcellulose, low-substituted hydroxypropylcellulose, hypromellose (hydroxypropylmethylcellulose); and mixtures of these and similar ingredients.

A "lubricant" is an excipient added to reduce sticking by a solid formulation to the equipment used for production of a unit does form, such as, for example, the punches of a tablet press. Examples of lubricants include magnesium stearate and calcium stearate. Other lubricants include, but are not limited to, aluminum-stearate, talc, sodium benzoate, glyceryl mono fatty acid (e.g. glyceryl monostearate from Danisco, UK), glyceryl dibehenate (e.g. Comprito-lATO888™ Gattefosse France), glyceryl palmito-stearic ester (e.g. Precirol™, Gattefosse France), polyoxyethylene glycol (PEG, BASF) such as PEG 4000-8000, hydrogenated cotton seed oil or castor seed oil (Cutina H R, Henkel) and others.

A "diluent" is an excipient added to a pharmaceutical composition to increase bulk weight of the material to be formulated, e.g. tabletted, in order to achieve the desired weight.

The term "disintegrant" refers to excipients included in a pharmaceutical composition in order to ensure that the composition has an acceptable disintegration rate in an environment of use. Examples of disintegrants include starch derivatives (e.g., sodium carboxymethyl starch and pregelatinized corn starch such as starch 1500 from Colorcon) and salts of carboxymethylcellulose (e.g., sodium carboxymethylcellulose), crospovidone (cross-linked PVP polyvinylpyrrolidinone (PVP), e.g., Polyplasdone™ from ISP or Kollidon™ from BASF).

The term "glidant" is used to refer to excipients included in a pharmaceutical composition to keep the component powder flowing as a tablet is being made, preventing formation of lumps. Nonlimiting examples of glidants are colloidal silicon dioxides such as CAB-O-SIL™ (Cabot Corp.), SYLOID™, (W.R. Grace & Co.), AEROSIL™ (Degussa), talc, and corn starch.

The term "nonionic surfactant" refers to, for example and not limitation, sucrose esters; partial fatty acid esters of polyhydroxyethylenesorbitan, such as polyethylene glycol(20) sorbitan monolaurate, monopalmitate, monostearate and monooleate; polyethylene glycol(20) sorbitan tristearate and trioleate); polyethylene glycol(4) sorbitan monolaurate and monostearate; polyethylene glycol(5) sorbitan monooleate; polyhydroxyethylene fatty alcohol ethers such as polyoxyethylene cetyl stearyl ether or corresponding lauryl ethers; polyhydroxyethylene fatty acid esters; ethylene oxide/propylene oxide block copolymers; sugar ethers and sugar esters; phospholipids and their derivatives; and ethoxylated triglycerides such as the derivatives of castor oil. Examples include Cremophor™ RH 40; Cremophor™ RH 60, Tween™ 80.

The terms "over-coating," "over-coating layer," or "over-coat" refer to an outer most coating or coatings of a unit dose form such as a tablet or caplet, which may be added to improve appearance, taste, swallowability, or other characteristics of the tablet or caplet. The over-coating layer does not contain an API. Suitable over-coatings are soluble in, or rapidly disintegrate in water, and, for purposes of this invention, are not enteric coatings. An exemplary over-coating material is Opadry II available from Colorcon, Inc., Westpoint Pa.

"QD", "BID", "TID", "QID", and "HS" have their usual meanings of, respectively, administration of medicine once per day, twice per day, three times per day, four times per day or at bedtime. Administration three times per day means that at least 6 hours, preferably at least 7 hours, and more preferably about 8 hours elapse between administrations. Administration three times per day can mean administration about every 8 hours (e.g., 7 a.m., 3 p.m. and 11 p.m.). In some cases in which quantitative measurements are made, "TID administration" can mean administration every 8±0.25 hours.

As used herein, the term "daily quantity" refers to the quantity of an API (ibuprofen or famotidine) administered over a 24-hour period under a specific dosing regimen.

The term "barrier layer" refers a layer in the unit dosage form that is interposed between the ibuprofen-containing compartment (e.g., an ibuprofen core or coated ibuprofen particles) and the famotidine-containing compartment (e.g., famotidine-containing coating or coated famotidine particles). Generally, the barrier layer does not contain an API. A barrier layer of the invention may be a water-soluble, pH independent film that promotes immediate disintegration for rapid release of the coated drug (i.e., ibuprofen and/or famotidine). Usually a readily soluble film is used. Materials that can be used for readily soluble films are well known in the art and include cellulose derivatives such as hydroxypropylmethyl cellulose, hydroxypropyl cellulose, hydroxypropyl methylcellulose phthalate, cellulose acetate phthalate, and ethyl cellulose; methacrylic polymers, amino-alkylmethacrylate copolymers (e.g. Eudragit™ E), polyvinyl acetate phthalate and polyvinyl alcohol (PVA). A plasticizer (e.g., triacetin, diethyl phthalate, tributyl sebacate or polyethylene glycol) may also be included. The barrier layer may include an antiadherent or glidant (e.g., talc, fumed silica or magnesium stearate) and colorants such as titanium dioxide, iron oxide based colorants or others. In one embodiment the barrier layer comprises a non-toxic edible polymer, edible pigment particles, an edible polymer plasticizer, and a surfactant. Materials include, for example and not limitation, materials described in U.S. Pat. No. 4,543,370 (Colorcon), incorporated herein by reference. Exemplary barrier layers include OPADRY®, which is available from Colorcon (West Point Pa. USA); OPADRY II® which is available from Colorcon (West Point Pa. USA) and comprises HPMC, titanium dioxide, plasticizer and other components; and polyvinyl alcohol-polyethylene glycol copolymer marketed as Kollicoat® IR (BASF). Suitable barrier layers, for illustration and not limitation, include Kollicoat® IR (a polyvinyl alcohol-polyethylene glycol graft copolymer) and Kollicoat IR White® both manufactured by BASF Aktiengesellschaft (Ludwigshafen, Germany). The thickness of the barrier layer can vary over a wide range, but is generally in the range 20 to 3,000 microns, such as on the order of about 25 to 250 microns. Preferably the barrier layer retards the release of API by less than 5 minutes, preferably less than 4 minutes and more preferably by less than 3 minutes.

A "subject in need of ibuprofen treatment" is an individual who receives therapeutic benefit from administration of ibuprofen. Ibuprofen is indicated for treatment of mild to moderate pain, dysmenorrhea, inflammation, and arthritis. In one embodiment, the subject in need of ibuprofen treatment is under treatment for a chronic condition. For example and without limitation, a subject in need of ibuprofen treatment may be an individual with rheumatoid arthritis, an individual with osteoarthritis, an individual suffering from chronic pain (e.g., chronic low back pain, chronic regional pain syndrome, chronic soft tissue pain), or an individual suffering from a chronic inflammatory condition. In general, a subject under treatment for a chronic condition requires ibuprofen treatment for an extended period, such as at least one month, at least four months, at least six months, or at least one year. In another embodiment, the subject in need of ibuprofen treatment is under treatment for a condition that is not chronic, such as acute pain, dysmenorrhea or acute inflammation. Preferably the patient in need of ibuprofen treatment does not suffer from a condition characterized by hypersecretion of gastric acid (e.g., Zollinger-Ellison Syndrome). Preferably the patient does not suffer from Barrett's ulceration or active severe oesophagitis. In certain embodiments the subject does not have gastroesophageal reflux disease (GERD). In certain embodiments the subject is not in need of treatment for an ulcer. In certain embodiments the subject does not suffer from dyspepsia. In certain embodiments the subject is at elevated risk of developing an NSAID-induced ulcer. In some embodiments the subject has a Body Mass Index in the normal range.

An "ibuprofen responsive condition" is a condition for which symptoms are reduced by administration of ibuprofen, such as mild to moderate pain, dysmenorrhea, inflammation, arthritis (e.g., rheumatoid arthritis and osteoarthritis), chronic pain, chronic inflammatory condition, chronic pain, acute pain and acute inflammation.

A "subject in need of famotidine treatment" is an individual who receives therapeutic benefit from administration of famotidine. In one embodiment, the subject in need of famotidine treatment requires treatment for non-ulcerative dyspepsia. In one embodiment, the subject in need of famotidine treatment requires treatment for gastroesophageal reflux disease (GERD) or for esophagitis due to GERD or for ulcer (duodenal or gastric). In one embodiment, the subject does not take ibuprofen for treatment of a chronic condition. In one embodiment, the subject is not under NSAID therapy (e.g., does not take ibuprofen and/or a different NSAID for treatment of a chronic condition). In one embodiment, the subject in need of famotidine treatment requires treatment for dyspepsia but does not require treatment for ulcer, GERD or its complications. As used herein, "subject in need of famotidine treatment" specifically excludes any subject in need of treatment for hypersecretion of gastric acid (e.g., Zollinger-Ellison Syndrome). In certain embodiment, the patient does not suffer from Barrett's ulceration or active severe oesophagitis. In certain embodiments a "subject in need of famotidine treatment" does not suffer from gastroesophageal reflux disease (GERD) or esophagitis due to GERD. In certain embodiments a "subject in need of famotidine treatment" does not have an ulcer. In certain embodiments the subject does not suffer from dyspepsia.

A "famotidine responsive condition" is a condition for which symptoms are reduced by administration of famotidine, such as dyspepsia, GERD, esophagitis due to GERD, or ulcer.

A subject is "at elevated risk for developing an NSAID-induced ulcer" if the subject in more susceptible than the average individual to development of an ulcer when under treatment with an NSAID. A high odds ratio for risk of development of NSAID-associated ulcer complications is seen in individuals with a past complicated ulcer (odds ratio 13.5), individuals taking multiple NSAIDs or NSAIDs plus aspirin (odds ratio 9.0); individuals taking high doses of NSAIDs (odds ratio 7.0), individuals under anticoagulant therapy, such as low dose aspirin (odds ration 6.4), individuals with a past uncomplicated ulcer (odds ratio 6.1), and individuals older than 70 years (odds ratio 5.6) See, e.g., Gabriel et al., 1991, *Ann Intern Med*. 115:787; Garcia Rodriguez et al. 1994, *Lancet* 343:769; Silverstein et al. 1995, *Ann Intern Med*. 123:241; and Sorensen et al., 2000, *Am J Gastroenterol*. 95:2218. Subjects at increased risk for developing an NSAID-induced ulcer may have one or more of these risk factors. Subjects "at high risk for developing an NSAID-induced ulcer" are individuals older than 80 years of age and subjects with a history of NSAID-associated serious gastrointestinal complications (e.g., perforation of ulcers, gastric outlet obstruction due to ulcers, gastrointestinal bleeding).

"Admixture" refers to a pharmaceutical composition made by combining and mixing two or more drugs and one or more excipients in the same compartment of a unit dosage form.

A "compartment" in the context of a unit dosage form is a physical region of a tablet or other dosage form. Two components of a unit dosage form are in "separate compartments" when they are physically separated (e.g., by a barrier layer).

As used herein in the context of a unit dosage form, the term "enteric" has its usual meaning and refers to a medicinal preparation that passes through the stomach intact and disintegrates in the intestine. An "enteric coating" remains insoluble at gastric pH, then allows for release of the active ingredient from a coated particle or coated dosage form at pH greater than about 5.0, e.g., greater than pH 5.5, 6.0, 6.5, or 7.0

As used herein, "dyspepsia" refers to upper abdominal pain or discomfort with or without symptoms of early satiety, nausea, or vomiting with no definable organic cause, as diagnosed following the Rome II criteria (Talley et al., 1999, *Gut* 45 (Suppl. II):1137-42), or any subsequent modification thereof. According to the Rome II criteria, a diagnosis of functional dyspepsia requires: (1) persistent or recurrent abdominal pain or discomfort centered in the upper abdomen; (2) symptom duration of at least 12 weeks, which need not be consecutive, within the preceding 12 months; (3) no evidence of organic disease (including at upper endoscopy) that is likely to explain symptoms; (4) no evidence that dyspepsia is exclusively relieved by defecation or association with the onset of a change in the stool frequency or stool form (i.e., not irritable bowel syndrome). In this context, "discomfort" is defined as an unpleasant sensation, and may include fullness, bloating, early satiety, and nausea. The definition includes, without limitation, ulcer-like, dysmotility-like, and non-specific dyspepsia. Symptoms of dyspepsia include nausea, regurgitation, vomiting, heartburn, prolonged abdominal fullness or bloating after a meal, stomach discomfort or pain, and early fullness.

A unit dose form is in an "aqueous environment" when it is in a water-based solution in vivo (e.g., in the stomach) or in vitro. One in vitro aqueous environment is 50 mM potassium phosphate buffer, pH 7.2. Another in vitro aqueous environment is 50 mM potassium phosphate buffer, pH 4.5.

As used herein, a person with "normal body weight" has a body mass index of 20-25 inclusive (calculated as weight (kg)/[height (m)]$^2$).

As used herein, a "24-hour dosing cycle" or "24-hour dosing period" refers to a 24-hour period of time during which a subject is administered drug(s) and may correspond to a calendar day (e.g., 12:01 a.m. to midnight) or may span two calendar days (noon day 1 to noon day 2).

All percentages are % w/w, unless specifically indicated otherwise. Unless otherwise indicated, "% weight" is percent weight of the specified component compared to the total weight of the unit dosage (e.g., tablet). Optionally the % weight can be calculated as if the total weight of the unit dosage form is the weight of the ibuprofen portion, famotidine portion, and barrier layer, but not including the overcoating (e.g., added to mask taste, improve ease of swallowing, to improve appearance, and the like). Optionally the % weight can be calculated based on the total weight of the unit dosage form, including all coatings. "United States Pharmacopeia" and "USP" mean the United States Pharmacopeia and National Formulary 29th Revision (available from 12601 Twinbrook Parkway, Rockville, Md. 20852-1790, USA). It will be appreciated that due to rounding or practical limits on quantitive measurements, reference to a quantity of API or excipient in a dosage form can include some variation, such as ±10%, preferably ±5%, and more preferably ±1%. It will be appreciated, for example, that a total quantity of 80 mg famotidine can be administered in three doses of 26.6 mg famotidine per dose.

7.0 TID Administration of Ibuprofen-Famotidine Oral Dosage Form

In one aspect the present invention relates to administration of an oral dosage form comprising ibuprofen, famotidine, and one or more pharmaceutically acceptable excipients, to a patient in need of ibuprofen treatment. In part, the present invention is directed to a method of reducing or preventing the occurrence of gastrointestinal toxicity associated with the use of ibuprofen, such as gastrointestinal ulceration and dyspepsia. In one embodiment, the invention is directed to a method for preventing toxicities associated with ibuprofen use in patients who are specifically at risk for the development of such toxicities.

When administered to avoid or mitigate the ulcerogenic effects of long-term NSAID therapy, famotidine is administered at 40 mg BID (see Taha et al., 1996, supra). However, it has now been determined using pharmacokinetic modeling (see Example 1) and in clinical trials (see Example 2) that, surprisingly, TID administration of famotidine provides a protective effect superior to that achieved by BID dosing. For example, TID administration of famotidine results in intragastric pH higher than 3.5 for a greater proportion of the dosing cycle than conventional BID dosing.

Unexpectedly, treatment using the methods of the present invention result in reduced interpatient variability with respect to gastric pH in a population of patients receiving an ibuprofen-famotidine combination treatment. This reduction increases predictability of the treatment and reduces the likelihood that any particular patient will experience detrimental gastric pH in the course of ibuprofen-famotidine combination treatment.

In addition, a human clinical study described in Example 3, below, has shown that the pharmocokinetic parameters for concurrent administration of immediate release forms of ibuprofen and famotidine were not significantly different from pharmacokinetic parameters for separate administration of the two APIs. When administered concurrently, both ibuprofen and famotidine retain immediate release characteristics of rapid absorption and rapid attainment of the maximum plasma concentration ($T_{max}$).

These data indicate that a treatment paradigm in which ibuprofen and famotidine are administered as a unit dose form on a TID (three times per day) schedule will deliver ibuprofen that is bioequivalent to that of conventional TID dosing of ibuprofen, while providing significant and superior protection from ibuprofen-related side effects such as increased likelihood ulcer development and dyspepsia. Administration of ibuprofen-famotidine TID will provide superior protection, as measured by gastric pH, compared to cotherapy with famotidine BID and ibuprofen TID.

Thus, in one aspect, the present invention provides a method for administration of ibuprofen to a patient in need of ibuprofen treatment by administering an oral dosage form comprising a therapeutically effective amount of ibuprofen and a therapeutically effective amount of famotidine, where the oral dosage form is administered three times per day (TID). The invention also provides oral unit dosage forms adapted for use in this method.

8.0 Incompatibility of Ibuprofen and Famotidine

It has been discovered that, under "forced degradation" conditions, ibuprofen and famotidine in admixture are pharmaceutically incompatible. Forced degradation conditions refer to conditions of elevated temperature, or elevated temperature and humidity, intended to accelerate the process of chemical degradation. Forced degradation conditions for a period of time are used to predict the effect of storage under more benign conditions (e.g., room temperature) for a longer period of time. The present invention overcomes this incompatibility by formulating the ibuprofen and famotidine in separate compartments of the dosage form.

Thus in one aspect, the present invention provides a method for administration of ibuprofen to a patient in need of ibuprofen treatment by administering an oral dosage form comprising a therapeutically effective amount of ibuprofen and a therapeutically effective amount of famotidine, wherein the oral dosage form is administered three times per day (TID), and wherein the ibuprofen and the famotidine are in separate compartments of the oral dosage form. The invention also provides oral unit dosage forms adapted for use in this method.

Surprisingly, however, in certain formulations ibuprofen and famotidine are stable in admixture at room temperature. Thus, alternatively, the invention overcomes the incompatibility of ibuprofen and famotidine by selection of the formulation components (see, e.g., Example 4 and exemplary unit dose form VII, below).

9.0 Ibuprofen-Famotidine Oral Dosage Forms: API Content, Dissolution Properties and Protective Properties Exemplary formulations that may be used in the practice of the invention are described below.

9.1 API Content

The dosage forms of the invention comprise ibuprofen and famotidine in amounts sufficient to provide therapeutic efficacy when administered three times per day. At each administration time, a single unit dosage form (e.g., tablet) may be administered, or the appropriate amount of drug can be administered as a split dose (e.g., the same amount of drug administered as two tablets taken together). For example, TID administration of 800 mg ibuprofen and 26.6 mg famotidine can be in the form of a single unit dosage form containing 800 mg ibuprofen and about 26.6 mg famotidine, two unit dosage forms containing 400 mg ibuprofen and about 13.3 mg famotidine, or even four unit dosage forms containing 200 mg ibuprofen and about 7 mg famotidine. Preferably, a therapeutically effective dose is administered as one or two tablets.

The therapeutically effective amount of ibuprofen so administered is usually in the range 50 mg to 1000 mg. A therapeutically effective dose for headache or mild pain may be 200 mg or 400 mg TID. A therapeutically effective dose for arthritis is usually 800 mg TID.

In general, the unit dosage forms of the invention comprise ibuprofen in an amount of about 50-1000 mg. In certain embodiments the unit dosage form comprises ibuprofen in an amount of about 200-800 mg, about 300-500 mg, about 700-800 mg, about 400 mg or about 800 mg ibuprofen.

For many applications the quantity of ibuprofen in the unit dose form is about 800 mg (e.g., in the range 750 mg to 850 mg) which allows administration of 2400 mg/day with TID administration of one tablet, or the quantity of ibuprofen is about 400 mg (e.g., in the range 375 mg to 425 mg) which allows administration of 2400 mg/day with TID administration of two tablets.

The therapeutically effective amount of famotidine so administered is usually in the range 7 mg to 30 mg. In general, the unit dosage forms of the invention comprise famotidine in the range of 12 mg to 28 mg. For many applications the quantity of famotidine in the unit dose form is about 26.6 mg (e.g., in the range 24 mg to 28 mg) which allows administration of 80 mg/day with TID administration of one tablet, or the quantity of famotidine is about 13 mg (e.g., in the range 12 mg to 14 mg) which allows administration of 80 mg/day with TID administration of two tablets.

In one preferred embodiment, the oral unit dosage forms are formulated to deliver a daily dose of about 2400 mg ibuprofen and about 80 mg famotidine with three times per day administration. For many applications the quantity of ibuprofen is about 800 mg (e.g., in the range 750 mg to 850 mg) and the quantity of famotidine is about 26.6 mg (e.g., in the range 24 mg to 28 mg). This allows administration of 2400 mg/day ibuprofen and 80 mg/day famotidine with TID administration of one tablet. In a related embodiment, the quantity of ibuprofen is about 400 mg (e.g., in the range 375 mg to 425 mg) and the quantity of famotidine is about 13 mg (e.g., in the range 12 mg to 14 mg). This allows administration of 2400 mg/day ibuprofen and 80 mg/day famotidine with TID administration of two tablets. In a related embodiment, the quantity of ibuprofen is about 200 mg (e.g., in the range 175 mg to 225 mg) and the quantity of famotidine is about 6.6 mg (e.g., in the range 6 mg to 7 mg).

In one embodiment, the oral unit dosage forms are formulated to deliver a daily dose of about 1800 mg ibuprofen and about 80 mg famotidine with three times per day administration. For many applications the quantity of ibuprofen is about 600 mg (e.g., in the range 550 mg to 650 mg) and the quantity of famotidine is about 26.6 mg (e.g., in the range 24 mg to 28 mg). This allows administration of 1800 mg/day ibuprofen and 80 mg/day famotidine with TID administration of one tablet. In a related embodiment, the quantity of ibuprofen is about 300 mg (e.g., in the range 275 mg to 325 mg) and the quantity of famotidine is about 13 mg (e.g., in the range 12 mg to 14 mg). This allows administration of 1800 mg/day ibuprofen and 80 mg/day famotidine with TID administration of two tablets.

In other embodiments more or less API may be administered. For example, in some cases the daily dose of ibuprofen is greater than 2400 mg (e.g., 3200 mg). This amount can easily be administered as, for example, three or six tablets per day, particularly using an ibuprofen formulation that can be tabletted with little excipient (e.g., BASF Ibuprofen DC 85®). If a formulation that contains only the active S-enantiomer of ibuprofen is used, a smaller quantity may sometimes be administered (e.g., an amount that produces the same therapeutic effect as a therapeutic dose of the racemic mixture).

In certain embodiments the ratio of ibuprofen to famotidine in the dosage forms of the invention is in the range of 15:1 to 40:1, more often 20:1 to 40:1, and even more often 25:1 to 35:1. In some embodiments the ratio of ibuprofen to famotidine in the dosage forms of the invention is in the range of 29:1 to 32:1, such as 30:1 to 31:1. In one embodiment the ratio of ibuprofen to famotidine is about 30:1. Exemplary amounts of ibuprofen and famotidine include 800±10% mg ibuprofen and 26.6±10% mg famotidine; 400±10% mg ibuprofen and 13.3±10% mg famotidine; and 200±10% mg ibuprofen and 6.65±10% mg famotidine.

In certain embodiments the ratio of ibuprofen to famotidine in the dosage forms of the invention is in the range of range of 20:1 to 25:1, such as 22:1 to 23:1. In one embodiment the ratio of ibuprofen to famotidine is about 22.5:1. Exemplary amounts of ibuprofen and famotidine include 600±10% mg ibuprofen and 26.6±10% mg famotidine.

In a preferred embodiment, the oral dosage form does not contain a pharmaceutically active compound (i.e., drug compound) other than ibuprofen and famotidine. In particular embodiments the oral dosage form does not contain any NSAID other than ibuprofen and/or does not contain any H2-receptor antagonist other than famotidine. In certain embodiments the amount of famotidine is other than 5 mg, other than 10 mg, other than 20 mg or other than 40 mg per dosage form.

9.2 Rapid Release of Famotidine and Ibuprofen

In certain embodiments oral dosage forms of the invention are formulated so that release of both APIs occurs (or begins to occur) at about the same time. "At about the same time" means that release of one API begins within 5 minutes of the beginning of release of the second API, sometimes with 4 minutes, sometimes within 3 minutes, sometimes within 2 minutes, and sometimes essentially simultaneously. "At about the same time" can also mean that release of one API begins before release of the second API is completed. That is, the dosage form is not designed so that one of the APIs is released significantly later than the other API. For example, the barrier layer (described below), if present, is not designed to significantly delay release of the API contained within it. Combinations of excipients (which may include one or more of a binder, a lubricant, a diluent, a disintegrant, a glidant and other components) are selected which do substantially retard release of an API. See e.g., HANDBOOK OF PHARMACEUTICAL MANUFACTURING FORMULATIONS, 2004, Ed. Sarfaraz K Niazi, CRC Press; HANDBOOK OF PHARMACEUTICAL ADDITIVES, SECOND EDITION, 2002, compiled by Michael and Irene Ash, Synapse Books; and REMINGTON SCIENCE AND PRACTICE OF PHARMACY, 2005, David B. Troy (Editor), Lippincott Williams & Wilkins.

In some embodiments both the famotidine or ibuprofen are formulated for immediate release, and not for release profiles commonly referred to as delayed release, sustained release, or controlled release. For example, in an embodiment the unit dosage form is formulated so that famotidine and ibuprofen are released rapidly under neutral pH conditions (e.g., an aqueous solution at about pH 6.8 to about pH 7.4, e.g., pH 7.2). In this context "rapidly" means that both APIs are significantly released into solution within 20 minutes under in vitro assay conditions. In some embodiments both APIs are significantly released into solution within 15 minutes under in vitro assay conditions. In this context, "significantly released" means that at least about 60% of the weight of the API in the unit dosage form is dissolved, preferably at least about 75%, more preferably at least about 80%, often at least 90%, and sometimes at least about 95%. In one embodiment, both famotidine and ibuprofen are at least 95% released in 30 minutes.

Dissolution rates may be determined using known methods. Generally an in vitro dissolution assay is carried out by placing the famotidine-ibuprofen unit dosage form(s) (e.g., tablet(s)) in a known volume of dissolution medium in a container with a suitable stirring device. Samples of the medium are withdrawn at various times and analyzed for dissolved active substance to determine the rate of dissolution. Dissolution may be measured as described for ibuprofen in the USP or, alternatively, as described for famotidine in the USP. One approach is illustrated in Example 6. Briefly, the unit dose form (e.g., tablet) is placed in a vessel of a United States Pharmacopeia dissolution apparatus II (Paddles) containing 900 ml dissolution medium at 37° C. The paddle speed is 50 RPM. Independent measurements are made for at least three (3) tablets. In one suitable in vitro assay, dissolution is measured using a neutral dissolution medium such as 50 mM potassium phosphate buffer, pH 7.2 ("neutral conditions") generally as described in Example 6, below.

9.3 Substantial Release of Famotidine and Ibuprofen Under Low pH Conditions

In an embodiment the unit dosage form is formulated so that famotidine and ibuprofen are both released rapidly under low pH conditions. Release under low pH conditions is measured using the assay described above and in Example 6, but using 50 mM potassium phosphate buffer, pH 4.5 as a dissolution medium. As used in this context, the APIs are released rapidly at low pH when a substantial amount of both APIs is released into solution within 60 minutes under low pH assay conditions. In some embodiments, a substantial amount of both APIs is released into solution within 40 minutes under low pH assay conditions. In some embodiments, a substantial amount of both APIs is released into solution within 20 minutes under low pH assay conditions. In some embodiments, a substantial amount of both APIs is released into solution within 10 minutes under low pH assay conditions. In this context, a "substantial amount" means at least 15%, preferably at least 20%, and most preferably at least 25% of ibuprofen is dissolved and at least 80%, preferably at least 85%, and most preferably at least 90% of famotidine is dissolved.

9.4 Gastric Protection

As illustrated in Examples 1 and 2, TID administration to a subject of famotidine results in an intragastric pH that is elevated (in magnitude and/or duration), on average, relative to the intragastric pH resulting from conventional BID administration of famotidine, resulting in better gastric protection. As used herein administration of a pharmaceutical composition or compositions "provides better gastric protection" compared to administration of a reference composition or compositions when administration of the pharmaceutical composition maintains stomach pH at a more basic level. It has now been discovered that TID administration of famotidine provides better gastric protection than conventional BID dosing of the same daily dose of drug.

Intragastric pH can be determined by art-known methods using, for example, a nasogastric pH probe. One useful probe is the Digitrapper™ pH 400 ambulatory pH recorder from Medtronic Functional Diagnostics (Shoreview, Minn.). Typically pH is measured several times minute (e.g., the Digitrapper™ pH 400 makes measurements at a frequency of ¼ Hz) and the median pH over a 24 hour period is calculated. Measurements can be calculated for specific periods (e.g., upright, sleeping, postprandial, etc). Measurements can be made after the subject has received the appropriate dosage regimen for 1, 2 or 3 days or longer than 3 days, such as after several weeks of use.

An individual in need of ibuprofen treatment and receiving ibuprofen-famotidine combination therapy will have greater gastric protection when a unit dose containing famotidine (or containing a famotidine plus ibuprofen combination) is administered TID. Similarly, in a group of treated individuals in which responses are somewhat variable, an individual may have a reduced likelihood of gastric damage (e.g., exposure to low pH) when an ibuprofen-famotidine unit dose form is administered TID. The individual (or individuals in a group) may in some cases have shared characteristics. In general the individual or individuals (hereinafter, "individual") is an adult (over 18 years of age). In one embodiment the individual is male. In one embodiment the individual is female. In one embodiment the individual has an age in the range 19-42 years. In various embodiments the individual may have an age in years in the range of 20-30, 25-35, 30-40, 35-45, 40-50, 45-55, 50-60, 55-65, 60-70 or older than 70 years old. In one embodiment the individual has a normal weight (i.e., a Body Mass Index of 20-25). In one embodiment the individual does not have a normal body weight (i.e., BMI<20 or BMI>25).

Gastric protection can be measured in a single individual or in a group of individuals (a "patient population"). Measurements can be made in a specified group of individuals to measure gastric protection (e.g., to determine the median gastric pH) and the median of the measure of gastric protection (e.g., time with gastric pH>4; median pH over 24 hour period, etc.) determined. In one embodiment the individuals in the group are male. In one embodiment the individuals in the group are female. In one embodiment the group includes both male and female individuals. In one embodiment the group includes both individuals under treatment for RA. In various embodiments the individuals in the group may have an age in years in the range of 19-42, 20-30, 25-35, 30-40, 35-45, 40-50, 45-55, 50-60, 55-65, 60-70 or older than 70 years old. In one embodiment the individuals in the group have a normal weight (i.e., a Body Mass Index of 20-25). In another embodiment, a patient population is a group of patients who are under the care of the same doctor or healthcare provider or receive treatment at the same health care facility or obtain therapeutics at the same pharmacy.

9.4.1 Fraction of 24-hour dosing cycle with pH above a specified value

One measure of gastric protection is the fraction of a 24-hour dosing cycle during which amount of time pH is maintained above a designated value (e.g., pH 2.5, pH 3.0, pH 3.5, pH 4.0, or pH 4.5). For example, better gastric protection can be characterized as pH above the designated value for more time in a 24 hour dosing cycle than administration of the reference composition(s). TID administration of famotidine (or, alternatively a unit dosage form of the invention containing famotidine and ibuprofen) will maintain gastric pH of 2.5 or greater for at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23 hours of a 24 hour dosing cycle. In one embodiment, TID administration of famotidine (or, alternatively a unit dosage form of the invention containing famotidine and ibuprofen) will maintain a gastric pH of 3.0 or greater for at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23 hours of a 24 hour dosing cycle. In one embodiment, TID administration of famotidine (or, alternatively a unit dosage form of the invention containing famotidine and ibuprofen) will maintain a gastric pH of 3.5 or greater for at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23 hours of a 24 hour dosing cycle. In one embodiment, TID administration of famotidine (or, alternatively a unit dosage form of the invention containing famotidine and ibuprofen) will maintain a gastric pH of 4.0 or greater for at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23 hours of a 24 hour dosing cycle. TID administration of famotidine (or, alternatively a unit dosage form of the invention containing famotidine and ibuprofen) will maintain gastric pH of 4.5 or greater for at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, or at least 23 hours of a 24 hour dosing cycle. In one embodiment of the present invention, TID administration of famotidine (or, alternatively TID administration a unit dosage form of the invention containing famotidine and ibuprofen) results in a gastric pH above a specified value (e.g., at least 2.5, at least 3.0, at least 3.5, at least 4.0 or at least 4.5) for more time in a 24-hour dosing cycle that than BID administration of the same daily dose of famotidine (or, alternatively a BID administration of the same daily dose of famotidine and TID administration of the same daily dose of ibuprofen) where the difference is (in minutes) at least 10, at least 20, at least 30, at least 40, or at least 50, at least 60, at least 120, at least 180, at least 240, at least 300 or more.

9.4.2 Minimum sustained gastric pH

Another measure of gastric protection is the minimum sustained gastric pH during a 24-hour dosing cycle. "Sustained pH" refers to a gastric pH (or pH range) sustained for at least 10 minutes. Better gastric protection can be characterized as a higher minimum sustained pH when measured over a 24-hour dosing period. In one embodiment of the present invention, TID administration of famotidine (or, alternatively a unit dosage form of the invention containing famotidine and ibuprofen) results in a minimum sustained pH of at least 2.0, preferably at least 2.3, more preferably at least 2.5, and sometimes at least 3.0. In one embodiment of the present invention, TID administration of famotidine (or, alternatively TID administration a unit dosage form of the invention containing famotidine and ibuprofen) results in a minimum sustained pH that is higher than BID administration of the same daily dose of famotidine (or, alternatively a BID administration of the same daily dose of famotidine and TID administration of the same daily dose of ibuprofen) where the difference in pH is at least 0.2, at least 0.4, at least 0.5, at least 0.6, or at least 0.7 pH units.

9.4.3 Median gastric pH

Another measure of gastric protection is the median gastric pH during a 24-hour dosing cycle. Better gastric protection can be characterized as a higher median gastric pH over a 24-hour dosing period. In one embodiment of the present invention, TID administration of famotidine (or, alternatively a unit dosage form of the invention containing famotidine and ibuprofen) results in a median gastric pH of at least 2.5, at least 2.6, at least 2.7, at least 2.8, at least 2.9, at least 3.0, at least 3.1, at least 3.2, at least 3.3, at least 3.4, at least 3.5, at least 3.6, at least 3.7, at least 3.8, at least 3.9, at least 4.0, at least 4.1, at least 4.2, at least 4.3, at least 4.4, at least 4.5, at least 4.6, at least 4.7, at least 4.8, at least 4.9, at least 5.0, at least 5.1, at least 5.2, at least 5.3, at least 5.4, at least 5.5, at least 5.6, at least 5.7, at least 5.8, at least 5.9, at least 6.0, at least 6.1, at least 6.2, at least 6.3 or at least 6.4.

In one embodiment of the present invention, TID administration of famotidine (or, alternatively TID administration a unit dosage form of the invention containing famotidine and ibuprofen) results in a median gastric pH that is higher than BID administration of the same daily dose of famotidine (or, alternatively a BID administration of the same daily dose of famotidine and TID administration of the same daily dose of ibuprofen) where the difference in pH is at least 0.2, at least 0.3, at least 0.4, at least 0.6, at least 0.7 or at least 0.8 pH units.

For illustration, TID administration of a unit dosage form containing 800 mg ibuprofen and 26.6 mg famotidine would provide superior gastric protection than does TID administration of a unit dosage form containing 800 mg ibuprofen and BID administration of a unit dosage form containing 40 mg famotidine.

9.5 Reduced Patient-to-Patient Variability

As shown in Example 2, interpatient variability in gastric pH was significantly reduced when subjects received 80 mg/day famotidine as three 26.7 mg doses (TID administration) compared to two 40 mg doses (BID administration).

It is known that there may be considerable patient-to-patient variability in the effects of drugs or drug combination administered to a population of patients. This interpatient variability complicates the treatment of many disorders, and identifying methods to reduce side-effects (toxicity) and maximize effectiveness in a diverse population is challenging. In the case of subjects receiving ibuprofen and famotidine treatment in combination, the interpatient variation means that some patients have heightened susceptibility to side-effects resulting from low gastric pH. Methods that reduce interpatient variability should therefore reduce the incidence of side-effects in the treated population. That is, reducing inter-patient variability in a group reduces the risk that any particular individual in the group will experience detrimental gastric pH.

In one aspect, the present invention provides a method for reducing interpatient variability with respect to gastric pH in a population of patients receiving an ibuprofen-famotidine combination treatment, by administering an oral dosage form containing a therapeutically effective amount of ibuprofen and a therapeutically effective amount of famotidine, where the oral dosage form is administered three times per day (TID). In one embodiment the population of patients in which interpatient variability is reduced comprises all patients in need of or receiving ibuprofen-famotidine combination therapy. In this context, "ibuprofen-famotidine combination therapy" refers to administration of ibuprofen and famotidine as part of the same course of treatment which, as noted above, generally involves administration of ibuprofen TID and administration of famotidine BID. In other embodiments the population of patients in which interpatient variability is reduced comprises a subpopulation of patients in need of or receiving ibuprofen-famotidine combination therapy such as individuals having a Body Mass Index in the range of 20-25 and/or having an age in years in the range of 19-42, 20-30, 25-35, 30-40, 35-45, 40-50, 45-55, 50-60, 55-65, or 60-70.

The observed reductions in interpatient variability provides important clinical benefits. These important clinical benefits include fewer patients who experience a daily median pH below 2.5 It is believe patients experiencing a median pH below 2.5 are at higher risk for gastric acid-induced ulceration when treated TID compared to BID dosing. Notably, as discussed in Example 2, infra, in a clinical study a 24-hour median gastric pH was below 2.5 for three patients when receiving famotidine on a BID schedule, but no patients when receiving famotidine on a TID schedule.

10.0 Exemplary Unit Dose Forms

Oral dosage forms of the invention may have a variety of designs, provided the ibuprofen and the famotidine are in separate compartments of the oral dosage form.

In some embodiments, the ibuprofen and the famotidine compartments are separated by a barrier layer. In some embodiments, the invention provides a solid oral dosage form with a first portion comprising a therapeutically effective amount of ibuprofen and a second portion comprising a therapeutically effective amount of famotidine, where the ibuprofen portion completely surrounds the famotidine portion or the famotidine portion completely surrounds the ibuprofen portion; and a barrier layer disposed between the two portions.

The API content of the unit dose forms is selected so that TID administration delivers a therapeutically effective dose of ibuprofen and a therapeutically effective dose of famotidine. Preferably the oral dosage form comprises ibuprofen and famotidine in the amounts and ratios described herein.

According to the invention, famotidine and ibuprofen are released rapidly, as described above. It will be recognized, therefore, that in this aspect of the invention neither the dosage nor the APIs individually are enteric coated or formulated for sustained or delayed release. The tablets are formulated so that they disintegrate in the stomach after they are swallowed and do not dissolve in the mouth or throat during the normal process of oral administration. Other properties of the oral dosage forms of the invention will be apparent to the reader.

With these properties in mind, exemplary oral dosage forms are described below, for illustration and not for limitation. It will be understood that many other forms may be made by one of skill in the art guided by this disclosure, and that information related to one dosage form below (e.g., a description of excipients) may be used in connection with other forms.

10.1 Exemplary Oral Dosage Form I

In one version, the oral dosage form comprises an ibuprofen core ("core"), a surrounding layer containing famotidine ("famotidine layer") and a barrier layer interposed between the core and famotidine layer. In one embodiment famotidine coat entirely surrounds the ibuprofen core. Optionally the tablet is coated by one or more over-coating layers, for example, to improve appearance, taste, swallowability, or for other reasons. Methods for formulation and manufacture of pharmaceutical unit dose forms are known in the art, see, e.g., HANDBOOK OF PHARMACEUTICAL MANUFACTURING FORMULATIONS, 2004, Ed. Sarfaraz K Niazi, CRC Press; HANDBOOK OF PHARMACEUTICAL ADDITIVES, SECOND EDITION, 2002, compiled by Michael and Irene Ash, Synapse Books; and REMINGTON SCIENCE AND PRACTICE OF PHARMACY, 2005, David B. Troy (Editor), Lippincott Williams & Wilkins. One of ordinary skill in the art guided by this disclosure will be able to make a variety of suitable oral unit dose forms.

10.1.1 The Ibuprofen Core of Exemplary Oral Dosage Form I

The ibuprofen core may vary in shape and may be, for example, round, ovoid, oblong, cylindrical (e.g., disk shaped) or any other suitable geometric shape, for example rectilinear. Preferably the tablet has a disk or ovoid shape is shaped like a flattened disk, ovoid or torpedo. The edges of the tablets may be beveled or rounded. The tablet may also be shaped as a caplet (capsule form tablet). The tablets may be scored, embossed or engraved. In one embodiment, the core does not have an internal hole extending all or part-way through the pill. For example, in one embodiment the core is not shaped like a cup or donut.

The tablet of the invention comprises a therapeutically effective amount of ibuprofen API. This is usually in the range 50 mg to 1000 mg. For many applications the quantity of ibuprofen is about 800 mg (e.g., in the range 750 mg to 850 mg, or in the range 775-825 mg) which allows administration of 2400 mg/day with TID administration of one tablet, or the quantity of ibuprofen is about 400 mg (e.g., in the range 375 mg to 425 mg) which allows administration of 2400 mg/day with TID administration of two tablets. In addition to ibuprofen the core may contain excipients such as one or more disintegrants, binders, glidants, or lubricants. For example, the core may contain lactose (e.g., lactose monohydrate); colloidal silicon dioxide; sodium croscarmellose; hydroxy propyl methyl cellulose; silicified microcrystalline cellulose and/or magnesium stearate. In one embodiment ibuprofen core comprises ibuprofen, 20-30% (w/w) lactose monohydrate; 0.1 to 2% colloidal silicon dioxide; 3-7% crosscarmellose sodium; 1-3% hydroxy propyl methyl cellulose; 2-6% silicified microcrystalline cellulose (e.g., Prosolv SMCC 90) and 0.1-2% magnesium stearate. In some embodiments, the core does not contain a lubricant.

In one embodiment, the core comprises Ibuprofen DC 85 (BASF) which comprises 85% API, or a similar directly compressible ibuprofen formulation described in WO 2007/042445 (i.e., an ibuprofen formulation comprising 50 to 99% by weight crystalline ibuprofen, 1 to 15% of a highly dispersible adjuvant having a minimum surface of 100 m²/g, wherein at least 50% of the surface of the ibuprofen crystals is coated with the highly dispersible adjuvant, and 0 to 40% other adjuvants. Exemplary formulations using Ibuprofen DC 85, for illustration and not limitation, include:

1) Ibuprofen DC 85 (88.24% w/w); microcrystalline cellulose (7.76%); crosslinked sodium carboxymethylcellulose (3.00%); silica (0.05%); and magnesium stearate (0.50%);
2) Ibuprofen DC 85 (88.24% w/w); corn starch (7.76%); crosslinked sodium carboxymethylcellulose (3.00%); silica (0.05%) and magnesium stearate (0.50%);
3) Ibuprofen DC 85 (88.24% w/w); lactose (7.76%); crosslinked sodium carboxymethylcellulose (3.00%); silica (0.05%) and magnesium stearate (0.50%).

The core may be formed using art-known techniques including wet granulation, dry granulation, direct compression or any other pharmaceutically acceptable process. The appropriate amount of the ibuprofen formulation (i.e., the amount containing the unit dose of API) may be compression pressed into individual cores. Alternatively, the core may be formed by molding.

In one embodiment, the core portion is at least 50% ibuprofen by weight, preferably at least 60%, and more preferably at least 70%, and even more preferably at least 80% ibuprofen.

10.1.2 The Barrier Layer of Exemplary Oral Dosage Form I

The barrier layer may be composed of any of a variety of materials that (1) separate the core and famotidine layer and (2) rapidly disintegrate in an aqueous (e.g., gastric) environment so that the ibuprofen is rapidly released.

The barrier layer may comprise fillers, binders, disintegrants, lubricants, glidants, and the like, as known in the art. Suitable fillers for use in making the barrier layer, or a portion thereof, by compression include water-soluble compressible carbohydrates such as sugars, which include dextrose, sucrose, maltose, and lactose, sugar-alcohols, which include mannitol, sorbitol, maltitol, xylitol, starch hydrolysates, which include dextrins, and maltodextrins, In one embodiment, the ibuprofen cores are coated with Opadry II™ white (Colorcon Y-22-7719) according to manufacturer's instructions to a weight gain of 1.5-2.0% w/w. Other known barrier layer materials include hydroxypropyl methylcellulose phthalate, polyvinyl acetate phthalate, and cellulose acetate phthalate. In one embodiment, the barrier layer formulation will contain at least one coating layer polymer and a coating solvent (preferably water) used for processing and removed by drying. The coating layer polymer may be hydroxypropyl methylcellulose, polyvinyl alcohol (PVA), ethyl cellulose, methacrylic polymers or hydroxypropyl cellulose. A plasticizer (e.g., triacetin, diethyl phthalate, tributyl sebacate or polyethylene glycol) may also be included. The coating layer may include an anti-adherent or glidant (e.g., talc, fumed silica or magnesium stearate) and colorants such as titanium dioxide, iron oxide based colorants or others.

The thickness of the barrier layer can vary over a wide range, but is generally in the range 20 to 3,000 microns, such as on the order of about 25 to 250 microns. Preferably the barrier layer retards the release of API by less than 5 minutes, preferably less than 4 minutes and more preferably by less than 3 minutes.

The barrier layer may be formed by any method, including compression, molding, dipping, or spray coating.

10.1.3 The Famotidine Layer of Exemplary Oral Dosage Form I

The famotidine layer is applied over the barrier coat. The famotidine layer can be applied by compression, spray coating, or other methods. In a preferred embodiment, the famotidine layer is applied by spray coating a formulation containing famotidine and excipients such as polymers, plasticizers, and the like. In one example, famotidine is combined with Opadry II (Colorcon) and spray coated over the ibuprofen core or barrier layer.

The dosage form of the invention comprises a therapeutically effective amount of famotidine API. For many applications the quantity of famotidine is about 26.6 mg (e.g., in the range 24 mg to 28 mg) which allows administration of 80 mg/day with TID administration of one tablet, or the quantity of famotidine is about 13 mg (e.g., in the range 12 mg to 14 mg) which allows administration of 80 mg/day with TID administration of two tablets.

10.1.4 Over Coating Layers of Exemplary Oral Dosage Form I

In some embodiments, the tablets are coated for oral administration, to make the tablet easier to swallow, to mask taste, for cosmetic reasons, or for other reasons. Coating of tablets and caplets is well known in the art. Coating systems are typically mixtures of polymers, plasticisers, coloring agents and other excipients, which can be stirred into water or an organic solvent to produce a dispersion for the film coating of solid oral dosage forms such as tablets.

Usually a readily soluble film is used. Materials that can be used for readily soluble films include cellulose derivatives (such as hydroxypropylmethyl cellulose) or amino-alkylmethacrylate copolymers (e.g. Eudragit™ E). Suitable coat layers, for illustration and not limitation, include Kollicoat® IR (a polyvinyl alcohol-polyethylene glycol graft copolymer) and Kollicoat IR White® both manufactured by BASF Aktiengesellschaft (Ludwigshafen, Germany).

10.2 Exemplary Oral Dosage Form II

In one version, the oral dosage form comprises many small particles of ibuprofen, each coated with a barrier layer, with the particles situated in a matrix or medium containing famotidine. The barrier layers may be made as described above (e.g., using Kollicoat™, Opadry™ or similar materials). In this version the particles may have a variety of sizes, ranging from a mean or average size of 200 microns to 2000 microns or more. For example, and not for limitation, the mean size can be in the range 200-1500, 600-700, 700-800, 800-900, 900-1000, 1100-1200, 1200-1300, 1300-1400, 1400-1500, 1500-1600, 1600-1700, 1700-1800, 1800-1900, 1900-2000 microns or more. In one embodiment at least 80%, and more often at least 90% of the particles are in the size range of 350-800 microns. In some embodiments a mixture of particle sizes is used. The ibuprofen particles may be contained in or distributed in a matrix containing famotidine. The matrix can include binders, lubricants, diluents, disintegrants, and other components known in the art. As used in this context, the term "matrix" does not connote any particular structure.

In one version, the ibuprofen particles can be contained in a capsule that also contains famotidine and suitable excipients or carriers.

10.3 Exemplary Oral Dosage Form III

In one version, the oral dosage form comprises many small particles of famotidine coated with a barrier layer and situated in a matrix containing ibuprofen. The barrier layers may be made as described above (e.g., using Opadry or similar materials). In certain versions, the particles may have a variety of sizes, ranging from a mean or average size of 100 microns to 2000 microns or more. For example, and not for limitation, the particles can be in the range 200-800, 200-600, 200-400, 350-800, or 350-600. In some embodiments a mixture of particle sizes is used. The matrix or tablet can include binders, lubricants, diluents, disintegrants, and other components known in the art. In one embodiment the matrix consists primarily of ibuprofen. In one embodiment the ibuprofen is Ibuprofen DC 85™ (BASF). In one version, the famotidine particles can be contained in a capsule that also contains ibuprofen and suitable excipients or carriers.

In one version, the unit dose form comprises coated famotidine particles mixed with ibuprofen (which may be Ibuprofen DC 85™) and compressed into tablets. In one approach the coated famotidine particles are prepared by spray granulating famotidine onto a carrier particles, coating the resulting granule with a barrier layer, and optionally a further protective layer.

In certain embodiments, the carrier particles may be an inert material such as microcrystalline cellulose (fine grade; e.g., Avicel PH101 [FMC Corp.]), or the like. The famotidine may be spray granulated onto the carrier particles in any suitable manner, e.g., in a fluid bed processor, using a solution of famotidine, an optional film former, an optional anti-static agent, and other optional excipients and diluents. For instance, Opadry II® or similar materials, e.g., such as those described in U.S. Pat. No. 4,802,924, incorporated herein by reference, may be used as a film former, and talc or similar inert material may be used as an anti-static agent. By way of non-limiting example, the famotidine spray mixture may comprise about 75% active, about 20% film former, and about 5% anti-static agent, by weight.

The famotidine spray mixture is coated onto the inert material until the desired amount of famotidine is added, such as a weight gain per particle or on a batch basis of 20% to 200%. For example, the 1.25 parts famotidine mixture can be sprayed on 1 part microcrystalline cellulose to a weight gain of about 90% to 110% (i.e., about 100%).

A barrier layer may be applied over the famotidine coated granules. Again, the barrier layer of the famotidine particles may be made as described above (e.g., using Opadry®, Kollicoat®, or similar materials). In certain embodiments, the barrier layer may be applied to about a 5-50% weight gain per particle or on a batch basis, e.g., a 20% weight gain.

In certain embodiments, the optional polymeric protective coating may be applied to about a 5%, 10%, 20%, or more than 20% weight gain per particle on a batch basis, depending on the degree of protective elastic/compressibility properties desired.

The resulting famotidine granules are preferably large enough for convenient handling and to maximize content uniformity of the resulting unit dose forms. In some embodiments the famotidine granules are in the size range of 100 microns to 1000 microns, such as in the range of 350-800 microns. Particle size is usually determined based on the ability of particles to pass through an opening (e.g., using a US sieve series, or Tyler equivalent mesh). In one embodiment at least about 80%, and usually at least 90%, of the famotidine particles are in the size range of less than 800 microns, e.g., 350-800 microns.

Particle size can be determined by microscopy, laser diffraction, dynamic light scanning (DLS), sieve analysis, or other methods. In a preferred embodiment particle size is determined by sieve analysis. Sieve analysis methods are routine in the art. For example, sieve analysis can be preformed using an ATM sonic sifter. The equipment may be set to run for 10 minutes with sift and pulse at amplitude #6. Sieves may be nested in the following order: #20 mesh (850 microns), #20 mesh (420 microns), #60 mesh (250 microns), #120 mesh (125 microns), #325 mesh (45 microns), and fines pan (<45 microns). Samples are run in duplicate and the generated percent retained reflect the average of the two measurements The famotidine particles may then be blended with ibuprofen granules and compressed into tablets in any suitable method known in the art. Optionally a lubricant, such as magnesium stearate, may be added to the ibuprofen-famotidine mixture prior to the compression step.

In one version the ibuprofen is in the form of granules with a mean particle size under 100 microns (e.g., 25, 38, 50, or 90 microns). Suitable ibuprofen preparations are available from BASF Aktiengesellschaft, Ludwigshafen, Germany. In one version the ibuprofen is in the form of an ibuprofen containing active agent preparation as described in patent publication US 20030045580 (assigned to BASF A.G.). In one version the ibuprofen is in the form of an ibuprofen preparation as described in patent publication US 20050003000 (assigned to BASF A.G.). In one version, the unit dose form contains coated famotidine granules, ibuprofen and excipients. Excipients may include binders (e.g., SMCC), lubricants (e.g., magnesium stearate), diluents, disintegrants (e.g., croscarmellose), coatings, barrier layer components, glidants (e.g., colloidal silicon dioxide). In one version a nonionic surfactant having an hydrophiliclipophilic balance (HLB) of at least 9 is included in the product (see, e.g., U.S. Pat. No. 6,251,945).

In one version the ibuprofen is in the form of the product DC 85 (BASF Aktiengesellschaft, Ludwigshafen, Germany). DC 85 comprises ibuprofen (>80%), silica, croscarmellose sodium and cellulose and is supplied in the form of granules with a median size of about 700 microns (>90% in the range 300-1400 microns). Optionally DC 85 are used which have a size distribution similar to that of the famotidine granules (e.g., at least at least about 80%, sometimes at least 90%, and sometimes at least 95% of the DC 85 particles are in the size range of 350-800 microns in an embodiment in which the majority of famotidine particles lie in that size range). DC-85 ibuprofen particles of desired size can be obtained by milling.

In one version, the unit dose form contains coated famotidine granules, DC 85 ibuprofen and a lubricant such as magnesium stearate.

A final coating (e.g., Opadry®, Opadry II®, Kollicoat® or similar materials) may be applied using, e.g., a 48" Accella coata according to manufacturer's instructions, as generally recognized by those skilled in the art.

10.4 Exemplary Oral Dosage Form IV

In one version, the oral dosage form comprises many small particles of ibuprofen, each coated with a barrier layer, and many small particles of famotidine each coated with a barrier layer and situated in a matrix containing ibuprofen. The barrier layers may be the same or different. The two types of particles can be contained in a matrix or medium to give form to the unit dosage (e.g., tablet).

In one version, the ibuprofen particles and famotidine particles are contained in a capsule, optionally with excipients or carriers.

10.5 Exemplary Oral Dosage Form V

In one version, the oral dosage form comprises famotidine and Ibuprofen DC 85™ (BASF) or famotidine and a coated ibuprofen product made according to the method of U.S. Pat. No. 6,251,945. In this embodiment, a nonionic surfactant coating of the ibuprofen separates the ibuprofen portion from the famotidine portion of the dosage form. In one embodiment, the unit dosage consists essentially of famotidine, Ibuprofen DC 85™, and optionally an over-coating coat. In other embodiments, the oral dosage form comprises additional excipients.

10.6 Exemplary Oral Dosage Form VI

In one version, the oral dosage form comprises famotidine and ibuprofen in a bilayer tablet, with famotidine plus excipient in one layer and ibuprofen plus excipient in the second layer. Usually the two layers are separated by a barrier layer. Usually an over-coating is also present.

10.7 Exemplary Oral Dosage Form VII (Admixture Forms)

Exemplary unit dose forms I-VI, above, which are provided for illustration and not limitation, are characterized by having the ibuprofen and famotidine APIs in different compartments of the tablet. In an other aspect, unit dose forms of the invention comprise ibuprofen (or other NSAID) in admixture with famotidine and at least one excipient. The unit dose form may be a tablet, caplet, gelcap, or other form. In some embodiments the dosage form includes a core comprising the ibuprofen and famotidine, which core is surrounded by an over coating which may be added to improve appearance, taste, swallowability, or other characteristics of the dosage form. It is preferred that the solid formulation of the present invention is durable to usual external manipulation yet able dissolve at the acceptable rate.

In one embodiment, the solid tablet carrier contains at least one, and preferably at least two, of the following components: microcrystalline cellulose, croscarmellose sodium, lactose, magnesium stearate, hydroxypropyl cellulose, starch and talc. For example, the unit dose form may contain one or more of the following excipients: 5-15% microcrystalline cellulose, 0.5-5% croscarmellose sodium, 10-85% lactose, 0.5-5% magnesium stearate, 2-6% hydroxypropyl cellulose, 3-15% pregelatinized starch (e.g. starch 1500), and/or 1-10% talc. In one embodiment the unit dose form comprises all of the all of the above excipients. It is most preferred, in this embodiment, that the tablet formulation comprises a therapeutically effective amount of ibuprofen or its pharmaceutically acceptable salts, in combination with famotidine with pharmaceutically acceptable excipients in a pharmacokinetically effective ratio. In one embodiment the excipients include microcrystalline cellulose 5-15% by weight, croscarmellose sodium 0.5-5% by weight, lactose 10-85% by weight, magnesium stearate 0.5-5% by weight, hydroxypropyl cellulose 2-6% by weight, pregelatinized starch 3-15% by weight and talc 1-10% by weight.

In the formulations of the invention, the excipients are present in an amount sufficient to allow for release of the ibuprofen and famotidine from the tablet after administration to a subject in need of this therapeutic combination in a fashion allowing for absorption into the blood at a time and concentration such that the therapeutic effects match that of ibuprofen administered alone and that of famotidine administered alone. As described in Example 3, it was demonstrated in human clinical studies that there are no significant differences between the pharmacokinetic parameters for either ibuprofen or famotidine when administered alone compared to administration in combination. It was concluded that both ibuprofen and famotidine can be considered bioequivalent when administered in combination compared to separate administration.

In a different embodiment, the pharmaceutical composition comprises microcrystalline cellulose 5-10% by weight, croscarmellose sodium 1-4% by weight, lactose 20-75% by weight, magnesium stearate 1-3% by weight, hydroxypropyl cellulose 3-5% by weight, pregelatinized starch 5-10% by weight and talc 2-6% by weight.

In another embodiment, the dosage for comprises 60-80% ibuprofen; 1.5-3.0% famotidine; 9-11% microcrystalline cellulose; 2-4% silicified microcrystalline cellulose; and 0.5-2.5% croscarmellose sodium.

Preferably the formulation comprises 60-80% ibuprofen; 1.5-3.0% famotidine; 9-11% microcrystalline cellulose; 2-4% silicified microcrystalline cellulose; 1-3% low substituted hydroxylpropylcellulose; and 0.5-2.5% croscarmellose sodium.

In one embodiment the formulation comprises ibuprofen, famotidine, microcrystalline cellulose, pregelatinized starch, hydroxypropyl cellulose, low substituted hydroxypropyl cellulose, silicon dioxide, silicified microcrystalline cellulose, croscarmellose sodium and magnesium stearate.

In one embodiment the formulation comprises 60-80% ibuprofen; 1.5-3.0% famotidine; 9-11% microcrystalline cellulose; 0.5-1.5% pregelatinized starch, 0.2-1% hydroxypropyl cellulose, 1-3% low substituted hydroxypropyl cellulose, 0.2-1% silicon dioxide, 2-4% silicified microcrystalline cellulose; 0.5-2.5% croscarmellose sodium, and 0.5-2.9% magnesium stearate.

In one embodiment the formulation comprises 76-78% ibuprofen; 1.5-2.5% famotidine; 9-11% microcrystalline cellulose; 0.5-1.5% pregelatinized starch, 0.2-1% hydroxypropyl cellulose, 1-3% low substituted hydroxypropyl cellulose, 0.2-1% silicon dioxide, 2-4% silicified microcrystalline cellulose; 0.5-2.5% croscarmellose sodium, and 0.5-2.9% magnesium stearate.

In certain embodiments the microcrystalline cellulose is comprised of a first population of particles having a median particle size of about 50 microns (e.g., EMOCEL 50M) and a second population of particles having a median particle size of approximately 90 microns (e.g., EMOCEL 90M). In some embodiments, 50-micron particles are present in at least 10-fold excess, and sometimes at least a 20-fold excess, over 90-micron particles.

In certain embodiments the silicified microcrystalline cellulose (SMCC) is comprised of a first population of particles having a median particle size of about 50 microns (e.g., PROSOLV 50 from Penwest) and a second population of particles having a median particle size of approximately 90 microns (e.g., PROSOLV 90 from Penwest). In one embodiment, the two populations are present in approximately equal quantities. In experiments inclusion of SMCC and low substituted hydroxypropylcellulose in the formulation resulted in tablets with better compressibility.

In one embodiment the unit dose form has the following composition:

| | |
|---|---|
| Famotidine | 1.5-2.5% |
| Microcrystalline cellulose (median particle size 50 microns) | 9-10% |
| Starch (pregelatinzed) | 0.8-10% |
| Hydroxypropyl cellulose | 0.4-0.8% |
| Ibuprofen | 70-80% |
| Colloidal silicon dioxide | 0.05-0.10% |
| Microcrystalline cellulose (median particle size 90 microns) | 0.2-0.6% |

-continued

| | |
|---|---|
| Silicified microcrystalline cellulose (median particle size 50 microns) | 1-2% |
| Silicified microcrystalline cellulose (median particle size 90 microns) | 1-2% |
| Low substituted HPC | 1-2% |
| Croscarmellose sodium | 1-3% |
| Magnesium stearate | 2-2.9% |

In one embodiment the unit dose form has the following composition:

| | |
|---|---|
| Famotidine | 1.9% |
| Microcrystalline cellulose (median particle size 50 microns) | 9.6% |
| Starch (pregelatinzed) | 0.96% |
| Hydroxypropyl cellulose | 0.58% |
| Ibuprofen | 76.9% |
| Colloidal silicon dioxide | 0.08% |
| Microcrystalline cellulose (median particle size 90 microns) | 0.42% |
| Silicified microcrystalline cellulose (median particle size 50 microns) | 1.73% |
| Silicified microcrystalline cellulose (median particle size 90 microns) | 1.73% |
| Low substituted HPC | 1.54% |
| Croscarmellose sodium | 2.0% |
| Magnesium stearate | 2.5% |

In one embodiment the unit dose form has the following composition:

| | |
|---|---|
| Famotidine | 13.3 mg |
| Microcrystalline cellulose (median particle size 50 microns) | 50.7 mg |
| Pregelatinzed starch | 5 mg |
| Hydroxypropyl cellulose | 3 mg |
| Ibuprofen | 400.0 mg |
| Colloidal silicon dioxide | 0.4 mg |
| Microcrystalline cellulose (median particle size 90 microns) | 2.2 mg |
| Silicified microcrystalline cellulose (median particle size 50 microns) | 9.0 mg |
| Silicified microcrystalline cellulose (median particle size 90 microns) | 9.0 mg |
| Low substituted HPC | 8.0 mg |
| Croscarmellose sodium | 10.4 mg |
| Magnesium stearate | 13.0 mg |
| total | 524.0 mg |

In one embodiment the unit dose form has the following composition:

| | |
|---|---|
| Famotidine | 2.5% |
| Microcrystalline cellulose (e.g., Emcocel ® 50 M) | 9.7% |
| Pregelatinzed starch (e.g., Starch 1500) | 0.95% |
| Hydroxypropyl cellulose (e.g., Klucel EXF) | 0.57% |
| Ibuprofen 90 | 76.3% |
| Colloidal silicon dioxide | 0.08% |
| Microcrystalline cellulose (e.g., Emcocel ® 90 M) | 0.42% |
| Silicified microcrystalline cellulose (e.g., ProSolv SMCC ® 50) | 1.72% |
| Silicified microcrystalline cellulose (e.g., ProSolv SMCC ® 90) | 1.72% |
| Low substituted HPC (e.g., LH-11) | 1.53% |
| Croscarmellose sodium | 2.0% |
| Magnesium stearate | 2.5% |

It has been discovered that, under "forced degradation" conditions, ibuprofen and famotidine in admixture are pharmaceutically incompatible. This incompatibility has commercial disadvantages in that tablet content may change over time. As shown in Example 4, below, famotidine alone is stable when stored for 2 weeks at 60° C., but is degraded when stored as a mixture with ibuprofen for 2 weeks at 60° C. or for 1 month at 40° C. and 75% relative humidity. Similarly, famotidine degradation is seen when a famotidine-ibuprofen admixture in the form of a tablet is stored 1 month at 60° C. Surprisingly, however, the tablet form is stable at room temperature for at least 4 months. This suggests that contrary to the conclusion that would be drawn from conventional stress testing, ibuprofen-famotidine tablets according to the invention are stable for a prolonged period under normal storage conditions.

10.8 Exemplary Method of Manufacture of an Embodiment of Oral Dosage Form I

It is within the ability of one of ordinary skill in the art, guided by the present disclosure and with reference to the pharmaceutical literature, to prepare and manufacture unit dosage forms of the invention.

For example, for illustration and not for limitation, in one approach an oral dosage form of Form 1 (above) uses wet granulation. A dry mix containing ibuprofen, a binder or binders (e.g., lactose monohydrate, hydroxy propyl methyl cellulose), disintegrant (e.g., crosscarmellose sodium) and glidant (e.g., colloidal silicon dioxide) is prepared. An aqueous solution containing a binder (e.g., hydroxy propyl methyl cellulose) is blended with the dry mix. The resulting wet material is milled and dried to form granules. The granules are blended with binder (e.g., silicified microcrystalline cellulose), disintegrant (e.g., crosscarmellose sodium), glidant (e.g., colloidal silicon dioxide) and lubricant (e.g., magnesium stearate). The final blend is compressed (e.g., using a DC 16 compression machine) to form the cores.

A barrier coat of Opadry II (Colorcon) is applied by spray coating according to the manufacturer's instructions. For example, one part Opadry II concentrate is added to four parts (by weight) distilled water with stirring to form a dispersion. The ibuprofen core tablets are placed in a rotating pan in a chamber where the temperature is maintained at 60-70° C. in order to control product temperature at 40-45° C. The famotidine-containing coating material is sprayed using a spray gun above the pan. (It can be expected that approximately 75% of the famotidine will coat the core, with about 25% lost during the coating process.) For example, and not for limitation, an Accela-Cota 60 inch pan equipped with four mixing baffles rotating at 5 rpm may be used. The spray apparatus may be the Five Spraying Systems 1/4 JAU air gun using 2850 fluid nozzles, 134255-45 aircaps and 60 psi atomizing air. The delivery system may be a pressure pot. The delivery rate may be 110 g/min/gun.

A famotidine layer can then be applied. A polymer containing famotidine can be applied to the coated core by, for example, spray coating or compression methods known in the art. In one approach, famotidine is mixed with Opadry II (Colorcon) in an about 1:1 ratio and applied generally as described above.

An overcoating layer can then be applied. In one embodiment, after the famotidine layer is applied, the unit dose forms are coated with Opadry II (Colorcon, Inc. West Point Pa.).

10.9 Exemplary Method of Manufacture of an Embodiment of Admixture Oral Dosage

A famotidine-ibuprofen tablet having suitable properties can be made using a wet granulation process and includes as components ibuprofen, famotidine, microcrystalline cellulose, silicified microcrystalline cellulose, and croscarmellose sodium.

In a related aspect, the invention provides methods for making ibuprofen/famotidine tablets with the above-described content and properties. In general it is desirable that tablets for oral administration have a high degree of uniformity as to weight and content, have dissolution properties appropriate for the API(s) being administered, and are chemically stable.

Methods for preparing tablets from a solid formulation are well known in the art. Briefly, tablets are usually formed by pressure applied to the material to be tabletted on a tablet press. A tablet press includes a lower punch which fits into a die from the bottom and an upper punch having a corresponding shape and dimension, which enters the die cavity from the top after the tabletting material fills the die cavity. The tablet is formed by pressure applied on the lower and upper punches. To prepare a tablet containing one or more active ingredients, the mixture to be compressed into the dosage forms should have certain physical characteristics for processing. Among other things, the mixture to be compressed must be free-flowing, must be lubricated, and must possess sufficient cohesiveness to ensure that the solid dosage form remains intact after compression. The ability of the material to flow freely into the die is important in order to provide for uniform filling of the die and continuous movement of the material from the source of the material, e.g. a feed hopper. The lubricity of the material is important in the preparation of the solid dosage forms in which the compressed material must be readily ejected from the punch faces.

Thus, compressibility and uniformity are important properties of a solid dosage formulation to be tabletted.

There are three general methods of preparation of materials to be included in a solid dosage form prior to compression: (1) direct compression; (2) dry granulation; and (3) wet granulation (including high shear mixer granulation and fluidized bed granulation).

In direct compression procedures, the materials to be included in the solid dosage form are compressed directly, without modifying the physical nature of the material itself. For solid dosage forms wherein the drug itself constitutes a substantial portion of the total weight of the solid dosage form, the use of direct compression is limited to those situations where the drug itself must exhibit physical characteristics, such as cohesiveness, that make it a good candidate for direct compression with the rest of the ingredients. Tablets containing famotidine as the sole active ingredient can be manufactured by direct compression. However, this approach is not ideal for manufacturing tablets comprising ibuprofen and famotidine, primarily due to the poor solubility and low cohesiveness of ibuprofen.

In dry granulation (also called "direct dry mixing") procedures, the tablet components are mixed, followed by slugging, dry screening, lubricating, and compression into tablets. Dry granulation may be used where one of the constituents, either the drug or the diluent, has sufficient cohesive properties to be tabletted. Tablets made by this process exhibited poor content uniformity for famotidine (84-87%) and a poor dissolution rate for famotidine (92-95% famotidine released after 30 minutes in a dissolution test).

Wet granulation procedures includes mixing the powders to be incorporated into a solid dosage form in an appropriate blender (such as a twin shell blender or double-code blender), and then adding solutions of a binding agent to the mixed powders to obtained a granulation. Thereafter, the damp mass is screened (e.g. in a 6-, 8-, 15-, 25-mesh screen), and dried (e.g. by tray drying, using a fluid-bed dryer, a spray dryer, microwave, vacuum, or infra-red dryer). A wet granulation approach to preparing ibuprofen/famotidine tablets is described in Examples 3-5 and was shown to be superior. Wet granulation provided a pre-compression material with better wetting properties, easing disintegration and dissolution. In addition, the content uniformity of the tablets prepared was improved.

In one aspect, the invention provides a method of making a tablet comprising ibuprofen and famotidine by:

a) preparing famotidine granules by wet granulation of 10 parts famotidine, 50 parts microcrystalline cellulose, 5 parts pregelatinized starch and 3 parts hydroxylpropyl cellulose, using water as the liquid, milling and screening the product;

b) mixing 400 parts ibuprofen and 0.4 parts colloidal silicon dioxide to produce intermediate mixture I;

c) mixing 2.2 parts microcrystalline cellulose, 9 parts SMCC 50, 9 parts SMCC90, 8 parts low substituted HPC, and 10.4 parts croscarmellose sodium to produce intermediate mixture II;

d) combining the intermediate mixture I and the famotidine granules incrementally by combining a first portion of intermediate mixture I with the famotidine granules and mixing, adding a second portion of intermediate mixture I and mixing, adding a third portion of intermediate mixture I and mixing, and optionally combining additional portions, thereby producing intermediate mixture III;

e) combining intermediate mixture II and intermediate mixture III to produce intermediate mixture IV;

f) adding 13 parts magnesium stearate to intermediate IV, thereby producing a ibuprofen/famotidine solid formulation; and, g) compressing the ibuprofen/famotidine solid formulation to form tablets.

Using the methods described herein the solid pharmaceutical compositions of the invention can be formed into tablets with at least about 90%, at least about 95% or at least about 97% content uniformity.

In one aspect, the invention provides a method of making a tablet comprising ibuprofen and famotidine by:

a) preparing famotidine granules by wet granulating famotidine in the presence of a binder and disintegrant and milling and screening the product;

b) mixing ibuprofen and a glident to produce an ibuprofen/glident mixture (intermediate mixture I);

c) mixing microcrystalline cellulose, silicified microcrystalline cellulose, low substituted HPC, and croscarmellose sodium (intermediate mixture II);

d) combining the famotidine granules with intermediate mixture II to produce intermediate mixture III;

e) combining intermediate mixture I and intermediate mixture III to produce intermediate mixture IV;

f) combining magnesium stearate to intermediate IV, thereby producing a ibuprofen/famotidine solid formulation; and, g) compressing the ibuprofen/famotidine solid formulation to form tablets.

In one embodiment, the famotidine granules in (a) are prepared by combining and blending famotidine, microcrystalline cellulose, pregelatinized starch and hydroxypropyl cellulose, adding water as the granulating liquid, drying the famotidine, and milling and screening the product.

In one embodiment, the glident in step (b) is colloidal silicon dioxide.

In one embodiment the invention provides a method of making a tablet comprising ibuprofen and famotidine by:
 a) preparing famotidine granules by wet granulation of 10 parts famotidine, 50 parts microcrystalline cellulose, 5 parts pregelatinized starch and 3 parts hydroxylpropyl cellulose, using water as the liquid, milling and screening the product;
 b) mixing 400 parts ibuprofen and 0.4 parts colloidal silicon dioxide to produce intermediate mixture I;
 c) mixing 2.2 parts microcrystalline cellulose, 9 parts SMCC 50, 9 parts SMCC90, 8 parts low substituted HPC, and 10.4 parts croscarmellose sodium to produce intermediate mixture II;
 d) combining the intermediate mixture I and the famotidine granules incrementally by combining a first portion of intermediate mixture I with the famotidine granules and mixing, adding a second portion of intermediate mixture I and mixing, adding a third portion of intermediate mixture I and mixing, and optionally combining additional portions, thereby producing intermediate mixture III;
 e) combining intermediate mixture II and intermediate mixture III to produce intermediate mixture IV;
 f) adding 13 parts magnesium stearate to intermediate IV, thereby producing a ibuprofen/famotidine solid formulation; and,
 g) compressing the ibuprofen/famotidine solid formulation to form tablets.

Using the methods described herein the solid pharmaceutical compositions of the invention can be formed into tablets with content uniformity (n=10) as shown below.

|  | Mean (% Claim) | RSD |
|---|---|---|
| Ibuprofen | 102.3 | 2.6% |
| Famotidine | 101.4 | 1.9% |

Dissolution results indicated at least 95% of ibuprofen or famotidine released after 10 minutes (measured under neutral dissolution conditions).

11.0 Packaging

In one aspect the invention provides a container, such as a vial, containing ibuprofen/famotidine unit dose forms of the invention, instructions to take the medication 3× daily are affixed to the container, or packaged with the container. In one embodiment the container contains a one-month supply of tablets (or other oral dosage form). In one embodiment, for example, the number of tablets in the container is from 89-94 tablets (e.g., 89, 90, 91, 92, 93 or 94 tablets). In one embodiment the number of tablets in the container is about 100 (e.g. 100±10). In a related aspect the invention provides a container containing a two-month supply of ibuprofen/famotidine tablets of the invention. The number of tablets in the container may be about 200 (e.g., 200±10) or may be in the range 178-188 tablets.

In a related aspect, the invention provides a container as described above, including instructions to take the medication 3× daily, except containing unit dose forms comprising famotidine and a non-ibuprofen NSAID as described herein (with a number of tablets as described above). In a related aspect, the invention provides a container as described above, including instructions to take the medication 3× daily, except containing unit dose forms comprising famotidine without any NSAID as described herein (with a number of tablets as described above).

12.0 TID Administration of Famotidine

Famotidine may be used for treatment (short term and maintenance) of duodenal ulcer, short term treatment of active benign gastric ulcer, gastroesophageal reflux disease (GERD), short term treatment of esophagitis due to GERD and has been administered to treat dyspepsia. At present famotidine is usually administered to BID or QD at a daily dose of 10, 20 or 40 mg. However, as demonstrated in Example 1, TID administration of famotidine provides better gastric protection than BID administration.

Thus, in an aspect, the invention provides a method for treatment of a famotidine-responsive condition by administering famotidine three times per day.

In one aspect, the invention provides a method for administering famotidine three times per day to treat or prevent NSAID-induced dyspepsia. While generally regarded as safe, a common side effect of NSAID administration is the development of upper gastrointestinal (GI) symptoms, such as dyspepsia. Among patients taking NSAIDs regularly dyspepsia is reported weekly in up to about 30% of patients and up to about 15% daily (see, e.g., Larkai et al., 1989, *J. Clin. Gastroenterol.* 11:158-62; Singh et al., 1996, *Arch. Intern. Med.* 156:1530-6). Thus, in one aspect, the invention provides a method of reducing symptoms of dyspepsia in a subject in need of NSAID treatment who has experienced symptoms of dyspepsia associated with NSAID administration, comprising administering to the subject an effective amount of a NSAID in combination with an effective amount of famotidine, wherein the famotidine is administered three times per day. The two drugs can be administered concurrently as separate formulations or combined as a single dosage form. In one embodiment the NSAID is ibuprofen. In various embodiments the subject requires treatment with the NSAID for at least one week, at least two weeks, at least one month, or at least three months.

13.0 Famotidine Unit Dose Forms Suitable for TID Administration

In an aspect of the invention, a unit dose form comprising famotidine and excipients is provided, where famotidine is the sole pharmaceutically active agent and the unit dose form contains famotidine sufficient to deliver a total daily dose of about 80 mg when administered on a TID schedule. In one version, for example, the quantity of famotidine is about 26.6 mg (e.g., in the range 24 mg to 28 mg) which allows administration of about 80 mg/day with TID administration of one tablet, or the quantity of famotidine is about 13 mg (e.g., in the range 12 mg to 14 mg, e.g., 13.3 mg) which allows administration of 80 mg/day with TID administration of two tablets. Other ranges and amounts are those described hereinabove for ibuprofen-famotidine unit dose forms.

In one embodiment famotidine is the only pharmaceutically active agent in the unit dose forms. In one embodiment the unit dose form does not contain an NSAID.

14.0 Famotidine-NSAID Dose Forms

In an aspect of the invention a unit dose form comprising famotidine, excipients and an NSAID is provided, where the famotidine content is sufficient to deliver a total daily dose of 70-85 mg, preferably 75-80 mg famotidine when administered three-times per day. Suitable NSAIDs include, without limitation, aspirin, diclofenac, meclofenamate, mefenamic acid, meloxicam, nabumetone, naproxen, oxaprozin, phenylbutazone, piroxicam, sulindac, tenoxicam, diflunisail, tiaprofenic acid, tolmetin, etodolac, fenoprofen, floctafenine, flurbiprofen, indomethacin, and ketoprofen, as well as ibuprofen. In one embodiment, the NSAID and famotidine are in separate compartments of the unit dose, rather than admixed. In one embodiment, the NSAID is formulated for modified- or sustained release (e.g., so that the NSAID is released over a period of about 8 hours).

15.0 Method of Treatment

In another aspect, the invention provides a method of treating a patient in need of ibuprofen treatment, comprising prescribing or administering the ibuprofen/famotidine unit dose forms (e.g., tablets) of the invention. In one embodiment the patient is instructed to ingest the drug tablets three times daily. In one embodiment the patient is instructed to ensure there is at least a 6-hr interval between administrations of consecutive doses.

In one aspect the invention provides a method of treating a patient in need of ibuprofen treatment, where the patient is at elevated risk for developing an NSAID-induced ulcer. In one aspect the invention provides a method of treating a patient in need of ibuprofen treatment, where the patient is at high risk for developing an NSAID-induced ulcer.

In one aspect the invention provides a method of reducing, in a subject in need of ibuprofen treatment, the risk of developing an ibuprofen-induced symptom or condition such as ulcer or GERD. This method involves administering to the subject an effective amount of a ibuprofen in combination with an effective amount of famotidine, wherein the famotidine is administered three times per day. In an embodiment, the ibuprofen and famotidine are administered as a single unit dosage form.

In one aspect the invention provides a method of reducing symptoms of a famotidine-responsive condition, such as dyspepsia, in a subject in need of NSAID treatment who has experienced symptoms of a famotidine-responsive condition, such as dyspepsia, associated with NSAID administration, by administering to the subject an effective amount of a NSAID in combination with an effective amount of famotidine, wherein the famotidine is administered three times per day. In an embodiment, the ibuprofen and famotidine are administered as a single unit dosage form.

In one aspect the invention provides a method of reducing symptoms of dyspepsia in a subject not taking an NSAID, by administering to the subject an effective amount of famotidine, wherein the famotidine is administered three times per day.

In a related aspect, the invention provides the use of famotidine in combination with ibuprofen for the manufacture of a medicament for treatment of an ibuprofen responsive condition, wherein said medicament is adapted for oral administration in a unit dosage form for administration three times per day. In a preferred embodiment, the unit dosage form has an amount of famotidine such that TID administration delivers about 80 mg famotidine per day (e.g., about 13 mg or about 26.6 mg per unit dose form). In a related aspect, the medicament has the form as described herein.

17.0 Business methods

Also provided is a business method comprising manufacturing, marketing, using, distributing, selling, or licensing, the ibuprofen-famotidine oral dosage forms of the invention. For example, the invention provides a method of doing business comprising (i) manufacturing ibuprofen/famotidine tablets of the invention, or having said tablets manufactured, and (ii) selling the ibuprofen/famotidine tablets to pharmacies or hospitals.

Also provided is a business method comprising manufacturing, marketing, using, distributing, selling, or licensing, the famotidine-only oral dosage forms of the invention. For example, the invention provides a method of doing business comprising (i) manufacturing famotidine tablets of the invention, or having said tablets manufactured, and (ii) selling the famotidine tablets to pharmacies or hospitals.

The invention also provides a method of doing business by advertising or selling a solid oral unit dosage form of the invention with instructions to take the dosage form on a TID schedule. In one embodiment the oral dosage form contains famotidine. In one embodiment the oral dosage form contains famotidine and ibuprofen.

The invention also provides a method of doing business by advertising or selling a solid oral unit dosage form of the invention with instructions to take the dosage form on a TID schedule.

18.0 EXAMPLES

18.1 Example 1

Administration of Famotidine TID Provides Superior Gastric Protection Compared to Administration of Famotidine BID Pharmocokinetic modeling shows that TID administration of famotidine and ibuprofen according to the method of the present invention provides protection superior to that achieved by conventional cotherapy. FIG. 1A shows the predicted effect on intragastric pH of administration of 26.6 mg famotidine TID. FIG. 1B shows the predicted effect on intragastric pH of administration of 40 mg famotidine BID. Modeling shows that over a twenty-four hour interval, intragastric pH is greater than 3.5 during for several more hours per day than achieved using TID administration of famotidine compared to conventional BID dosing. In FIG. 1, administration of 80 mg/day famotidine using TID dosing is shown to maintain pH greater than 3.5 for about 21 hours per twenty-four hour interval, while the same daily dose administered BID dosing maintains pH greater than 3.5 for about 17 hours per twenty-four hour interval. The precise duration of pH elevation can be confirmed in clinical trials and may deviate somewhat from the predicted values (with the TID dosing remaining more effective than the BID dosing).

Methodology: Mean plasma concentration versus time data from a single dose bioequivalence study (world wide web at fda.gov/cder/foi/anda/2001/75-311_Famotidine_Bioeqr.pdf, n=30) comparing 40 mg Pepcid and generic famotidine (Teva Pharm) were best fitted to a one compartment oral absorption model with a lag time using a nonlinear least-squares regression program, WinNonlin (Pharsight®). The following pharmacokinetic parameters for Pepcid were obtained:

| Parameter | Units | Estimate |
|---|---|---|
| V/F | L | 241.8 |
| $k_a$ | $h^{-1}$ | 0.8133 |

-continued

| Parameter | Units | Estimate |
|---|---|---|
| $k_{el}$ | $h^{-1}$ | 0.2643 |
| $T_{lag}$ | h | 0.3677 | where V/F is the apparent volume of distribution, $k_a$ is the absorption rate constant, $k_{el}$ is the elimination rate constant and $T_{lag}$ is the absorption lag time.

The relationship between plasma concentrations of Pepcid and intragastric pH in one patient were digitized from FIG. 4 of Echizen and Ishizaki, supra, page 189. The digitized plasma concentration vs. intragastric pH were fitted using a nonlinear least-squares regression program, WinNonlin to a sigmoid Emax model using the following equation:

$$E = E_o + \frac{E_{max} * C^\gamma}{EC_{50}^\gamma * C^\gamma}$$

where E is the intragastric pH at C, $E_o$ is the intragastric pH at time zero, $E_{max}$ is the maximum intragastric pH, $EC_{50}$ is the Pepcid concentration at one-half of Emax, C is the plasma concentration of Pepcid and γ is the shape factor. The estimated pharmacodynamic parameters are listed below:

| Parameter | Units | Estimate |
|---|---|---|
| $E_{max}$ | — | 7.80 |
| $EC_{50}$ | ng/mL | 32.6 |
| $E_0$ | — | 1.88 |
| γ | — | 4.80 |

Using the pharmacokinetic parameters obtained above together with the pharmacodynamic parameters above, plasma concentrations as well as intragastric pH as a function of time were simulated for various dose regimens.

18.2 Example 2

Administration of Famotidine TID Provides Superior Gastric Protection Compared to Administration of Famotidine BID A randomized, open-label, two-period, crossover study was carried out to compare the effects on gastric pH of administration of 80 mg per day of famotidine when administered for five consecutive days in two versus three divided doses each day.

A. Study Subjects

Thirteen healthy subjects participated in the study. The subjects' demographic parameters are provided in Tables 1 and 2.

TABLE 1

Baseline Demographic Information

9 Male
4 Female
Mean Age: 27.2 years
Range 19-42
Mean Body Mass Index*: 22.8
Range 19-27

*Body mass index (BMI) is calculated as weight (kg)/[height (m)]²

The normal range for BMI varies, however, 20-25 can be considered the normal range. Nine subjects had a BMI in the normal range ("Normal Weight group"), and four subjects (ID# 107, 111, 112 and 113) had a BMI outside of the normal range (Table 2).

TABLE 2

Baseline Demographic Information

| Subject # | Age | Gender | Body Mass Index |
|---|---|---|---|
| 102 | 22 | Female | 21 |
| 103 | 39 | Male | 22 |
| 104 | 27 | Female | 23 |
| 105 | 22 | Female | 22 |
| 106 | 23 | Male | 25 |
| 107 | 26 | Male | 19 |
| 108 | 42 | Male | 24 |
| 109 | 26 | Male | 23 |
| 110 | 29 | Male | 27 |
| 111 | 28 | Female | 19 |
| 112 | 19 | Male | 26 |
| 113 | 24 | Male | 22 |
| 201 | 27 | Male | 24 |

B. Study Protocol

Subjects were assigned randomly, in approximately a 1:1 ratio, to one of two, two-period treatment sequences as follows:

Treatment Sequence 1: 40 mg famotidine BID×5 days, followed by 26.6 mg famotidine TID×5 days.
Treatment Sequence 2: 26.6 mg famotidine TID×5 days, followed by 40 mg famotidine BID×5 days.

There was a washout of at least one week between administration of the last dose of Treatment Period 1 and administration of the first dose of Treatment Period 2.

PEPCID® (famotidine) for Oral Suspension (Merck & Co., Inc., 40 mg/5 mL) was administered with water. During treatment periods in which famotidine was administered TID, medication was administered at approximately 0800, 1600, and 2400 on each day of dosing. During treatment periods in which famotidine is to be administered BID, medication is administered at approximately 0800 and 2000 on each day of dosing.

All doses of study medication were administered orally, on an open-label basis. Subjects were prohibited from taking any medications or interventions that decrease gastric acid secretion or neutralize gastric acid, and any medications that are known or suspected to cause dyspepsia or gastrointestinal ulcers, throughout the study period.

Subjects were screened within 20 days prior to study entry and remained at the study center beginning at approximately 1500 h on Study Day 0 and continuing until approximately 1000 h on Study Day 6 of both treatment periods. (The first day of dosing for each treatment period is designated Study Day 1, and the last day of dosing is designated Study Day 2). Subjects were followed for 14 days after administration of their last dose of study medication.

Gastric pH was measured continuously, using a nasogastric pH probe, during the 24 hours following administration of the first dose of study medication on Study Day 1, and during the 24 hours following administration of the first dose of study medication on Study Day 5, during both treatment periods. Blood samples were collected prior to initiation of dosing, and prior to administration of the second dose of study medication on Study Day 1 and Study Day 5 during both treatment periods for determination of trough plasma famotidine concentrations. For each patient the median pH during a 24 hour period (or subperiod thereof) was calculated. To measure the effect of treatments for a group of individuals, the average or mean of the measured medians for several individuals was determined (i.e., average=$\{[M_1+M_2 \ldots M_x]/X\}$ where "x" is the number of individuals in the group and each "M" is the median for an individual in the group).

C. Results

Based on pH measurements made during the 24 hours following administration of the first dose of study medication on Study Day 1 during both treatment periods, TID dosing resulted in a higher gastric pH and less time of exposure to acidic conditions than BID dosing (measured as an average of measurements for all subjects or for subjects of normal weight). This result is consistent with the modeling in Example 1 showing that TID dosing provides better gastric protection. In addition, it was discovered that, surprisingly, there was significantly less patient-to-patient variation in response to treatment under the TID dosing regimen compared to the BID regimen.

i) Median Gastric pH

The median gastric pH over 24 hours (starting with the first administration of study drug) was measured. Table 3 shows the mean of 24 hour pH values for all subjects and compares the BID dosing regimen to the TID dosing regimen. The mean of the 24 hour value (medians) for all subjects for the BID dosing was 3.3 pH units compared to 3.6 units for the TID dosing. The 0.3 pH unit difference represents a 300% difference in activity of hydrogen ions.

TABLE 3

24 Hour pH Values

|  | BID | TID |
|---|---|---|
| Number | 13 | 13 |
| Mean | 3.3 | 3.6 |
| SD | 1.1 | 0.7 |
| Avr. Dev. | 0.9 | 0.6 |
| Range | 1.8-5.1 | 2.5-4.4 |
| Max-Min | 3.3 | 1.9 |

For the subset of subjects with a BMI in the normal range ("normal weight subjects") the difference between BID and TID was more pronounced, with a mean pH of 3.1 during the BID period and 3.6 during the TID period (Table 4). The 0.5 pH unit difference represents a 500% difference in activity of hydrogen ions.

TABLE 4

24 Hour pH Values for Normal Weight Subjects

|  | BID | TID |
|---|---|---|
| Number | 9 | 9 |
| Mean | 3.1 | 3.6 |
| SD | 1.1 | 0.7 |
| Avr. Dev | 0.9 | 0.5 |
| Range | 1.8-4.0 | 2.5-4.4 |
| Max-Min | 2.2 | 1.9 |

During the 24 hour pH measurement periods, pH values were recorded during a variety of conditions such as sitting upright, lying asleep, during meals and just after a meal. Each of these conditions affects the gastric pH in different manner. Specifically, measurements taken while upright tend to be more consistent due to the position of the pH probe while values taken during meals are altered due to the acidity of the food.

Table 5 presents the pH values taken while the subjects were in the upright position, the most reliable measure of gastric pH. As shown, the gastric pH during this period was 0.5 units higher for the TID dosing period compared to the BID dosing period. For the subset of normal weight subjects, the difference in pH during the upright period was 0.8 units (Table 6) with the TID dosing period having a higher mean pH than the BID dosing period.

TABLE 5 pH Values Taken in the Upright Position

|  | BID | TID |
|---|---|---|
| Number | 13 | 13 |
| Mean | 3.2 | 3.7 |
| SD | 1.2 | 0.8 |
| Avr. Dev. | 1.0 | 0.7 |
| Range | 1.8-5.1 | 2.3-4.7 |
| Max-Min | 3.3 | 2.4 |

TABLE 6

Upright pH Values for the Normal Weight Subjects

|  | BID | TID |
|---|---|---|
| Mean | 3.0 | 3.8 |
| SD | 1.0 | 0.9 |
| Avr. Dev. | 0.8 | 0.6 |
| Range | 1.8-4.6 | 2.3-4.7 |
| Max-Min | 2.8 | 2.4 |

SUMMARY

Mean gastric pH was higher during the first 24 hours of drug dosing during the TID arm than during the BID arm of the study.

TABLE 7

Amount By Which TID Dosing Provided Superior Gastric Protection Compared To BID Dosing (Mean of Group; Expressed as pH Units)

| Parameter measured | All Subjects | Normal Weight Group |
|---|---|---|
| Gastric pH (24 h) | 0.3 | 0.5 |
| Upright Gastric pH | 0.5 | 0.8 |

TABLE 8

Famotidine Effect on Gastric pH by Subject and Period

| Subject No. | Period | Drug type given | Median pH (24 hour) | Median pH (Upright) |
|---|---|---|---|---|
| 102 | 1 | TID 26.6 mg | 3.8 | 3.8 |
|  | 2 | BID 40 mg | 4.0 | 4.0 |
| 103 | 1 | BID 40 mg | 2.6 | 2.6 |
|  | 2 | TID 26.6 mg | 2.9 | 2.9 |
| 104 | 1 | TID 26.6 mg | 3.6 | 3.6 |
|  | 2 | BID 40 mg | 4.8 | 4.8 |
| 105 | 1 | TID 26.6 mg | 2.5 | 2.5 |
|  | 2 | BID 40 mg | 2.0 | 2.0 |
| 106 | 1 | TID 26.6 mg | 3.9 | 3.9 |
|  | 2 | BID 40 mg | 1.8 | 1.8 |
| 107 | 1 | BID 40 mg | 4.4 | 4.4 |
|  | 2 | TID 26.6 mg | 3.1 | 3.1 |
| 108 | 1 | BID 40 mg | 3.8 | 3.8 |
|  | 2 | TID 26.6 mg | 4.4 | 4.4 |

TABLE 8-continued

Famotidine Effect on Gastric pH by Subject and Period

| Subject No. | Period | Drug type given | Median pH (24 hour) | Median pH (Upright) |
|---|---|---|---|---|
| 109 | 1 | TID 26.6 mg | 4.0 | 4.0 |
| | 2 | BID 40 mg | 3.6 | 3.6 |
| 110 | 1 | TID 26.6 mg | 2.5 | 3.0 |
| | 2 | BID 40 mg | 2.1 | 2.1 |
| 111 | 1 | BID 40 mg | 5.1 | 5.1 |
| | 2 | TID 26.6 mg | 4.5 | 4.5 |
| 112 | 1 | BID 40 mg | 4.2 | 4.2 |
| | 2 | TID 26.6 mg | 3.1 | 3.1 |
| 113 | 1 | TID 26.6 mg | 4.4 | 4.4 |
| | 2 | BID 40 mg | 3.8 | 3.8 |
| 201 | 1 | BID 40 mg | 3.6 | 3.6 |
| | 2 | TID 26.6 mg | 4.5 | 4.5 | ii) Exposure to Gastric pH Below 3.5

Another important measure of benefit is the duration of time a subject spends during the 24 hour period with a gastric pH below certain critical values. The time spent below these values represents time during which the subject is at risk for complications such as gastric ulcers caused by gastric acid. The pH values that have been examined for this analysis are pH<3.5 (this section) and pH<4.0 (Section iii, below).

Tables 9-11 show the effect of dosing on the time gastric pH is below 3.5. Gastric pH was below 3.5 for 19.5 minutes less (on average) during the TID period compared to the BID dosing period (Table 9). For normal weight subjects gastric pH was below 3.5 for 89.3 minutes less during the TID period compared to the BID dosing period (Table 10).

TABLE 9

Time Below pH 3.5

| | BID | TID |
|---|---|---|
| Number | 13 | 13 |
| Average | 713.0 | 693.5 |
| SD | 211.7 | 152.2 |
| Avr. Dev. | 169.1 | 124.7 |
| Range | 459-1165 | 514-950 |
| Max-Min | 706 | 436 |

TABLE 10

Time Below pH 3.5 (Normal Weight Subjects)

| | BID | TID |
|---|---|---|
| Average | 752.0 | 662.7 |
| SD | 217.8 | 155.6 |
| Avr. Dev. | 175.1 | 116.7 |
| Range | 486-1165 | 514-950 |
| Max-Min | 679 | 436 |

TABLE 11

Total and Fraction Time pH < 3.5, by Subject and Period

| Subject No. | Period | Drug type given | Time pH < 3.5 (min) | Fraction time pH < 3.5 (%) |
|---|---|---|---|---|
| 102 | 1 | TID 26.6 mg | 681 | 47.3 |
| | 2 | BID 40 mg | 654 | 45.4 |
| 103 | 1 | BID 40 mg | 914 | 63.5 |
| | 2 | TID 26.6 mg | 845 | 58.7 |
| 104 | 1 | TID 26.6 mg | 700 | 48.7 |
| | 2 | BID 40 mg | 486 | 33.8 |
| 105 | 1 | TID 26.6 mg | 950 | 66 |
| | 2 | BID 40 mg | 1165 | 80.9 |
| 106 | 1 | TID 26.6 mg | 654 | 45.4 |
| | 2 | BID 40 mg | 965 | 67 |
| 107 | 1 | BID 40 mg | 560 | 38.9 |
| | 2 | TID 26.6 mg | 789 | 54.8 |
| 108 | 1 | BID 40 mg | 565 | 39.2 |
| | 2 | TID 26.6 mg | 463 | 32.1 |
| 109 | 1 | TID 26.6 mg | 578 | 40.1 |
| | 2 | BID 40 mg | 687 | 47.7 |
| 110 | 1 | TID 26.6 mg | 904 | 62.9 |
| | 2 | BID 40 mg | 907 | 63 |
| 111 | 1 | BID 40 mg | 459 | 31.9 |
| | 2 | TID 26.6 mg | 575 | 40 |
| 112 | 1 | BID 40 mg | 575 | 39.9 |
| | 2 | TID 26.6 mg | 784 | 54.4 |
| 113 | 1 | TID 26.6 mg | 514 | 35.7 |
| | 2 | BID 40 mg | 628 | 43.6 |
| 201 | 1 | BID 40 mg | 704 | 49.3 |
| | 2 | TID 26.6 mg | 579 | 40.2 | iii) Exposure to Gastric pH Below 4.0

Tables 12-14 show the effect of dosing on the time gastric pH is below 4.0. Gastric pH was below 4.0 for 23.1 minutes less (on average) during the TID period compared to the BID dosing period (Table 12). For subjects in the normal weight group gastric pH was below 4.0 for 89.9 minutes less during the TID period compared to the BID dosing period (Table 13).

TABLE 12

Time Below pH 4.0

| | TIME (Minutes) pH < 4 | |
|---|---|---|
| | BID | TID |
| Number | 13 | 13 |
| Average | 806.5 | 783.4 |
| SD | 204.0 | 138.4 |
| Avr. Dev. | 158.8 | 111.9 |
| Range | 514-1224 | 589-1048 |
| Max-Min | 710 | 459 |

TABLE 13

Time Below pH 4.0 (Normal Weight Subjects)

| | TIME (Minutes) pH < 4 | |
|---|---|---|
| | BID | TID |
| Average | 854.1 | 764.2 |
| SD | 202.1 | 145.2 |
| Avr. Dev. | 155.7 | 105.4 |
| Range | 714-1224 | 589-1048 |
| Max-Min | 510 | 459 |

TABLE 14

Total and Fraction Time pH < 4.0, by Subject and Period

| Subject No. | Period | Famotidine | Time pH < 4 (min) | Fraction time pH < 4 (%) |
|---|---|---|---|---|
| 102 | 1 | TID 26.6 mg | 767 | 53.2 |
|  | 2 | BID 40 mg | 714 | 49.6 |
| 103 | 1 | BID 40 mg | 1034 | 71.8 |
|  | 2 | TID 26.6 mg | 934 | 64.9 |
| 104 | 1 | TID 26.6 mg | 782 | 54.3 |
|  | 2 | BID 40 mg | 547 | 38.0 |
| 105 | 1 | TID 26.6 mg | 1048 | 72.8 |
|  | 2 | BID 40 mg | 1224 | 85.0 |
| 106 | 1 | TID 26.6 mg | 737 | 51.2 |
|  | 2 | BID 40 mg | 1005 | 69.8 |
| 107 | 1 | BID 40 mg | 640 | 44.4 |
|  | 2 | TID 26.6 mg | 855 | 59.4 |
| 108 | 1 | BID 40 mg | 841 | 58.4 |
|  | 2 | TID 26.6 mg | 589 | 40.9 |
| 109 | 1 | TID 26.6 mg | 718 | 50.0 |
|  | 2 | BID 40 mg | 803 | 55.8 |
| 110 | 1 | TID 26.6 mg | 962 | 66.0 |
|  | 2 | BID 40 mg | 961 | 66.7 |
| 111 | 1 | BID 40 mg | 514 | 35.7 |
|  | 2 | TID 26.6 mg | 644 | 44.7 |
| 112 | 1 | BID 40 mg | 683 | 47.4 |
|  | 2 | TID 26.6 mg | 857 | 59.5 |
| 113 | 1 | TID 26.6 mg | 658 | 45.7 |
|  | 2 | BID 40 mg | 763 | 53.0 |
| 201 | 1 | BID 40 mg | 756 | 52.5 |
|  | 2 | TID 26.6 mg | 645 | 44.8 |

TABLE 15

Summary

| | Mean reduction in time with gastric pH below critical value in subjects receiving drug TID compared to subjects receivng drug BID | |
|---|---|---|
| Parameter measured | All Subjects | Normal Weight Group |
| time <pH 3.5 | 19.5 min | 89.3 min |
| time <pH 4.0 | 23.1 min | 89.9 min | iv) Less Patient-to-Patient Variability

The data provided above demonstrate that when famotidine was administered TID, less subject-to-subject variation in gastric pH was observed than when famotidine was administered BID. As shown in Table 16 (compiled from Tables 3-15) the subject-to-subject variability is considerably less for TID dosing compared to BID dosing, as measured by standard deviation, average absolute deviation and range. For example, the range of 24 hour pH values for BID dosing was 1.8 to 5.1, or 3.3 pH units, between the minimum value and the maximum value. By comparison, the range was 2.5 to 4.4, or a 1.9 pH units, for TID dosing.

Decreased variability has important clinical implications. By extrapolation from these data, when famotidine (or famotidine and ibuprofen) is administered to a large population of patients, fewer patients will experience gastric pH levels markedly different from the group average. Thus, any individual patient treated with ibuprofen/famotidine according to the present invention is less likely to experience the detrimental effects of low gastric pH that would be the case with BID dosing of famotidine. That is, the incidence of side effects in a population treated according to the present invention can be expected to be lower than in an equivalent population receiving BID dosing.

TABLE 16

Reduced Subject-to-Subject Variability

| | BID | TID |
|---|---|---|
| pH Range (max-min) | 3.3 pH units | 1.9 pH units |
| Average Absolute Deviation | 0.9 | 0.5 |
| Standard Deviation | 1.1 | 0.7 |
| pH Range (max-min), normal weight subjects | 2.2 pH units | 1.9 pH units |
| Average Absolute Deviation | 0.9 | 0.5 |
| Standard Deviation | 1.1 | 0.7 |
| pH Range (max-min) in upright position | 3.3 pH units | 2.4 pH units |
| Average Absolute Deviation | 1.0 | 0.7 |
| Standard Deviation | 1.2 | 0.8 |
| pH Range (max-min) in Upright position, normal weight subjects | 2.8 pH units | 2.4 pH units |
| Average Absolute Deviation | 1.0 | 0.9 |
| Standard Deviation | 0.8 | 0.6 |
| Time below pH 3.5 range (min-max) | 706 min | 436 min |
| Average Absolute Deviation | 169.1 | 124.7 |
| Standard Deviation | 211.7 | 152.2 |
| Time below pH 3.5 range (min-max), normal weight subjects | 679 min | 436 min |
| Average Absolute Deviation | 175.1 | 116.7 |
| Standard Deviation | 217.8 | 155.6 |
| Time below pH 4.0 range (min-max) | 710 min | 459 min |
| Average Absolute Deviation | 158.8 | 111.9 |
| Standard Deviation | 204.0 | 138.4 |
| Time below pH 4.0 range (min-max), normal weight subjects | 510 min | 459 min |
| Average Absolute Deviation | 155.7 | 105.4 |
| Standard Deviation | 202.1 | 145.2 | v) Patient 106

As discussed above, for most of the subjects studied, TID dosing provided an increase in gastric protection, and this protection was accompanied by less patient-to-patient variability in response. Notably, the 24-hour median gastric pH was below 2.5 for three patients in the BID period, but for no patients in the TID period.

Response in individual patients varied, as is expected for administration of any drug regimen. The data in Table 17 illustrate that very significant differences in gastric protection may be seen in some patients.

TABLE 17

Subject 106 Summary

| Parameter | BID period | TID period | Difference |
|---|---|---|---|
| Median pH | 1.8 | 3.9 | 2.1 pH Units |
| Median pH (Upright) | 1.8 | 4.0 | 2.2 pH Units |
| Time pH < 4 | 1005 min | 737 min | 268 min |
| (% of 24-hour period) | (69.8%) | (51.2%) | | vi) Summary

It will be appreciated from this disclosure (see Examples 1-3) that administration of famotadine and ibuprofen according to the present invention results in one or more advantages over conventional administration:

1. Superior gastric protection when administered to a population of individuals (i.e., patients in need of ibuprofen treatment or famotidine treatment) especially populations of normal weight individuals.

2. Reduced interpatient variability when administered to a population of individuals resulting in a reduction in side-effects and improved safety.

3. High magnitude individual benefit in a subset of patients for whom gastric pH is substantially elevated using the methods of the invention when compared to BID dosing.

18.3 Example 3

Pharmacokinetic Drug-Drug Interaction Study of Ibuprofen and Famotidine in Healthy Male Subjects This example demonstrates that pharmocokinetic parameters of concurrent administration of ibuprofen and famotidine (as in the unit dose forms of the invention) are bioequivalent to separate administration of the two APIs. An open-label, randomized, single-dose, oral administration, two-period crossover study was conducted. Six male subjects were assigned randomly to Sequence 1 or Sequence 2:

Sequence 1
Period 1: 800 mg ibuprofen [Motrin®], followed 24 hr later by 40 mg famotidine [Pepcid®].
Period 2: Concurrent administration of 800 mg ibuprofen and 40 mg famotidine.
Sequence 2
Period 1: Concurrent administration of 800 mg ibuprofen and 40 mg famotidine.
Period 2: 800 mg of ibuprofen, followed 24 hr later by 40 mg famotidine.

Following administration of ibuprofen and famotidine plasma ibuprofen and/or famotidine concentrations were determined in samples collected predose and at 0.25, 0.5, 1.0, 1.5, 2, 4, 6, 8, 10, 12, 14, 18, and 24 hr after administration of ibuprofen and/or famotidine. Ibuprofen and famotidine plasma concentrations, and computed pharmacokinetic parameters, were listed and summarized by dose (mean, standard deviation, 95% confidence interval, minimum, maximum). Individual and mean (by time) concentration-versus-time curves for each treatment, plotted on a semi-log scale, were examined. Intra-subject comparisons were made between Period 1 and Period 2.

WinNonLin version 2.1 was used to analyze the pharmacokinetic parameters from the concentration-versus-time data based on a non-compartmental model. The pharmacokinetic values then were transferred to MS Excel or Graphpad Prism for calculation of means, SDs, confidence intervals, etc., for preparation of tables and figures, and for performance of statistical testing.

Analyses of variance appropriate for a two-period crossover design were performed on the computed parameters including terms for sequence, subject within sequence, formulation, and period. Analyses were performed on the observed data and on natural logarithm-transformed data for area under the concentration-versus-time curve (AUC) and maximum observed plasma concentration ($C_{max}$). Ninety-five (95) % confidence intervals were computed for the differences in treatment means.

After confirming the absence of a period effect for the pharmacokinetic parameters, individual AUC and $C_{max}$ data were pooled for each treatment (i.e., for both ibuprofen and famotidine administered alone and in combination) for bioequivalence testing. The individual data then were log-transformed (natural log) and the differences for each drug between administration alone versus in combination were determined for each subject. The means and 95% confidence intervals of these log-transformed differences were calculated, and the upper and lower bound of the log-transformed range were normalized and then tested for bioequivalence. These intervals were evaluated in relation to the criterion equivalence interval of 80% to 125% for log-transformed data. Tables 18-20 show the results of the analyses:

TABLE 18

Pharmacokinetic Parameters (mean ± SD, 95% CI) for Ibuprofen and Famotidine When Administered Alone and In Combination

| Parameter | Ibuprofen Alone | Ibuprofen With Famotidine | Famotidine Alone | Famotidine With Ibuprofen |
|---|---|---|---|---|
| $t_{max}$ (hr) | 1.58 ± 0.49 | 2.25 ± 1.89 | 1.67 ± 0.52 | 2.17 ± 0.93 |
| (95% CI) | (1.07-2.10) | (0.27-4.23) | (1.13-2.21) | (1.19-3.14) |
| $C_{max}$ | 56,279 ± 8,486 | 55,666 ± 12,106 | 143 ± 31 | 159 ± 50 |
| (ng/mL) | (47,374-65,184) | (42,961-68,370) | (111-175) | (107-211) |
| (95% CI) | | | | |
| $t_{1/2}$ (hr) | 2.50 ± 0.55 | 2.56 ± 0.59 | 3.66 ± 0.19 | 3.49 ± 0.35 |
| (95% CI) | (1.92-3.07) | (1.95-3.18) | (3.46-3.86) | (3.12-3.85) |
| $K_{el}$ | 0.29 ± 0.06 | 0.28 ± 0.06 | 0.19 ± 0.01 | 0.20 ± 0.02 |
| (95% CI) | (0.23-0.35) | (0.22-0.34) | (0.18-0.20) | (0.18-0.22) |
| $AUC_{(last)}$ | 236,992 ± 62,862 | 234,851 ± 67,655 | 883 ± 173 | 934 ± 275 |
| (ng/mL·hr) | (171,023-302,961) | (163,851-305,850) | (701-1064) | (646-1222) |
| (95% CI) | | | | |
| AUC | 245,124 ± 63,697 | 235,156 ± 67,749 | 893 ± 175 | 944 ± 279 |
| (ng/mL · hr) | (178,279-311,970) | (164,058-306,254) | (710-1077) | (651-1236) |
| (95% CI) | | | | |

TABLE 19

Bioequivalence Test Results for AUC (log-transformed values) for Ibuprofen and Famotidine When Administered Alone Versus In Combination

| Drug | $AUC_{(last)}$ Alone | $AUC_{(last)}$ In Combination | Difference | 95% CI |
|---|---|---|---|---|
| Ibuprofen | 12.35 | 12.33 | 0.02 | 0.94-1.11 |
| Famotidine | 6.765 | 6.799 | −0.034 | 0.79-1.19 |

[1]Test criterion: CI within 0.8-1.25

TABLE 20

Bioequivalence Test Results for $C_{max}$ (log-transformed values) for Ibuprofen and Famotidine When Administered Alone Versus In Combination

| Drug | $C_{max}$ Alone | $C_{max}$ In Combination | Difference | 95% CI |
|---|---|---|---|---|
| Ibuprofen | 10.93 | 10.91 | 0.02 | 0.85-1.23 |
| Famotidine | 4.94 | 5.02 | −0.08 | 0.76-1.12 |

[1]Test criterion: CI within 0.8-1.25

There were no significant differences between the treatment means for the pharmacokinetic parameters for either ibuprofen or famotidine when administered alone versus in combination. It was concluded that both ibuprofen and famotidine can be considered bioequivalent when administered in combination compared to separate administration.

18.4 Example 4

Trough concentrations of famotidine

Trough concentrations of famotidine were determined in blood samples from the subjects of the study described in Example 2. Samples were collected prior to initiation of dosing, and prior to administration of the second dose of study medication on Study Day 1 and Study Day 5 during both treatment periods. The results are presented in Table 21 below.

TABLE 21

Trough Plasma Concentration of Famotidine

| | Plasma Concentration of Famotidine (ng/mL) | | | |
|---|---|---|---|---|
| | 40 mg BID | | 26.6 mg TID | |
| | Day 1 | Day 5 | Day 1 | Day 5 |
| Mean | 10.5 | 15.7 | 9.7 | 15.7 |
| SD | 2.8 | 4.6 | 4.9 | 8.9 |

If more frequent dosing of famotidine led to plasma accumulation, the day 5 trough data for TID dosing would be significantly higher than the trough values for day 5 with BID dosing. As can be seen, the trough plasma values for the two dosing regimen were the same (15.7 ng/mL). It can be concluded from this that TID dosing does not lead to plasma accumulation of famotidine.

18.5 Example 5

Ibuprofen-Famotidine Compatibility Studies

As shown in Table 22, substantial degradation of famotidine was observed in the famotidine-ibuprofen mixture (1:29 ratio) under stress conditions in the presence of ibuprofen. In the absence of ibuprofen, famotidine is stable.

TABLE 22

Famotidine/Ibuprofen Stability Under Stress Conditions

| API | Storage condition | Famotidine Content* |
|---|---|---|
| Famotidine | 2 weeks at 60° C. | 98% |
| Famotidine + Ibuprofen | 2 weeks at 60° C. | 81% |
| Famotidine + Ibuprofen | 1 mo at 40° C./75% RH | 54% |

*Famotidine content was determined by analytical HPLC and expressed as percent of target content.

Similarly, as shown in Table 23 substantial degradation of famotidine was observed in the tablet dosage form containing ibuprofen in a tablet formulation under stress conditions. The tablets contained 10 mg famotidine, 800 mg ibuprofen and the following excipients: pregelatinized starch (Starch 1500); hydroxypropyl cellulose; colloidal silicon dioxide; microcrystalline cellulose (Emcocel®50M and 90M); SMCC (ProSolv® 50); SMCC (ProSolv® 90); low substituted HPC (LH-11); croscarmellose; sodium; and magnesium stearate. The tablets were prepared as described in Example 8-5 of U.S. Patent App. Pub. No. 2007-0043096 A1, which is incorporated by reference.

TABLE 23

Stability of Famotidine in Tablet Under Stress Conditions

| Drugs in Tablet Formulation | Storage Condition | Famotidine Content* |
|---|---|---|
| Famotidine (13.3 mg) + Ibuprofen (400 mg) | Initial | 100% |
| Famotidine (13.3 mg) + Ibuprofen (400 mg) | 1 week at 60° C. | 39% |
| Famotidine (13.3 mg) + Ibuprofen (400 mg) | 1 month at 40° C./75% RH | 83% |
| Famotidine (13.3 mg) + Ibuprofen (400 mg) | 2 months at 40° C./75% RH | 55% |
| Famotidine (13.3 mg) + Ibuprofen (400 mg) | 3 months at 40° C./75% RH | 32% |

*Famotidine content was determined by analytical HPLC and expressed as percent of target content.

TABLE 24A

Stability of Famotidine in Tablet (400 mg Ibuprofen, 10 mg Famotidine) Under Stress Conditions

| Stage Conditions | Amt. of Ibuprofen | Amt. of famotidine |
|---|---|---|
| 1 month at 25° C./60% RH | 100.3 | 98.8 |
| 8 months at ambient temp. | 101.4 | 97.3 |
| 1 week at 60° C. | 93.0 | 60.2 |
| 1 month at 60° C. | 99.1 | 4.1 |

"Amt. of ibuprofen/famotidine" refers to the amount of drug remaining at the end of the storage period (as % of original content). Drug content was determined by analytical HPLC.

In other studies, approximately 0.5 g famotidine API was mixed with 14.5 g ibuprofen. After grinding, API mixture was stored in glass vials under the conditions indicated. As shown in Table 24B, substantial degradation of famotidine was observed.

TABLE 24B

Famotidine/Ibuprofen Stability Under Stress Conditions

| API | Ibuprofen (% control) | | | Famotidine (% control) | | |
|---|---|---|---|---|---|---|
| Mixture | 1 wk 40° C. | 1 wk 60° C. | 2 wks 60° C. | 1 wk 40° C. | 1 wk 60° C. | 2 wks 60° C. |
| Famotidine | | | | 96.1 | 121.0 | 100.1 |
| Famotidine-Ibuprofen | 104.7 | 99.9 | 96.4 | 94.4 | 85.7 | 46.0 |

18.6 Example 6

Determination of Dissolution

One method for determination of the rate and extent of dissolution can be carried out using the methods described in the United States Pharmacopeia and National Formulary 29th Revision, under the following conditions:

| | |
|---|---|
| Dissolution Apparatus: | Apparatus II (Paddles) |
| Dissolution Medium: | 50.0 mM Potassium Phosphate Buffer, pH 7.2 |
| Dissolution Medium Volume: | 900 mL |
| Temperature in Vessel: | 37.0° C. ± 0.5° C. |
| Speed: | 50 RPM |
| Sampling Time: | 10 min., 20 min., 30 min., 45 min., 60 min., and infinity @ 250 rpm for 15 min. |
| Sampling Volume: | 1 mL |
| Sinker: | None |

When desired, the dissolution medium or other parameters may be varied. Typically a unit dose form is added to the vessel and dissolution is started. At specified times a portion (e.g., 2 ml) of medium is withdrawn and the amount of API in solution is determined using routine analytical methods (e.g., HPLC).

The assay above was used to determine the dissolution characteristics of a unit dose form prepared as described in Example 9 (following storage for 1 month 25° C./60% RH) with the result shown in Table 25.

TABLE 25

| | % Released | |
|---|---|---|
| Time (min) | Ibuprofen | Famotidine |
| 5 | 43.7 | 28.9 |
| 10 | 94.9 | 77.7 |
| 15 | 97.6 | 90.0 |
| 30 | 98.4 | 99.8 |
| 45 | 98.5 | 102.2 |
| 60 | 98.6 | 103.1 |
| 75 | 99.2 | 104.1 |

18.7 Example 7

Manufacture of Ibuprofen/Famotidine Unit Dose Forms

This example describes how to make a particular ibuprofen/famotidine unit dose form.

A. Producing the Ibuprofen Core

TABLE 26

| Item | Material | % w/w | mg/tablet | Function/Supplier |
|---|---|---|---|---|
| 1. | Ibuprofen USP | 64.00 | 800 | API/BASF |
| 2. | Lactose Monohydrate NF (80M) | 24.00 | 300 | Binder/Kerry Biosci. |
| 3. | Colloidal Silicon Dioxide NF (Cab-O-Sil M5P) | 0.48 | 6 | Glidant/Cabot |
| 4. | Croscarmellose Sodium NF Ac-di-Sol | 2.40 | 30 | Disintegrant/FMC |
| 5A. | Hypromellose USP, Methocel E-5 LV Premium (Intragranular in dry mix) | 1.44 | 18 | Binder/Dow |
| 5B | Hypromellose USP, Methocel E-5 LV Premium (Intragranular as solution) | 0.48 | 6 | Binder/Dow |
| 6. | Purified Water USP | — | q.s. | |
| 7. | Prosolv SMCC 90 (silicified microcrystalline cellulose) | 3.76 | 47 | Binder/JRS |
| 8. | Croscarmellose Sodium NF (Ac-di-Sol) | 2.40 | 30 | Disintegrant/FMC |
| 9. | Colloidal Silicon Dioxide NF (Cab-O-Sil M5P) | 0.32 | 4.0 | Glidant/Cabot |
| 10. | Magnesium Stearate NF | 0.72 | 9.0 | Lubricant/Peter Greven |
| | Core tablet weight | 100.0 | 1250 | |

Items 1-5A are sifted through Quadro Comil 16-mesh and mixed (Blend 1). Item 5B is dissolved in water and slowly added to Blend 1 using a mixer. Additional water is added and mixed. The wet material is dried at 50° C. for 12 h, milled using a 16-mesh screen with appropriate spacer, and dried until the LOD at 50° C. is below 0.5% w/w. Dried granules and extra granular material is transferred to a 3 cu. ft. V blender and mix for 3 minutes.

Items 7-9 are sifted through Quadro Comil using 16-mesh screen with appropriate spacer.

Item 10 (lubricant) is sifted through 30 mesh hand screen and transferred to the above blender and mixed for 3 minutes. The final blend is compressed into tablets using a DC 16 compression machine set with 0.3750×0.8125 caplet shaped punches. The target tablet weight is 1250 mg with range of 3.0% and hardness of 10-20 Kp.

B. Barrier Layer

The compressed tablets are coated with Opadry II white (Y-22-7719) according to manufacturer's instructions to a weight gain of 1.5-2.0% w/w.

C. Famotidine layer

Famotidine and Opadry II (Colorcon) are mixed at a 1:1 ratio and the unit dose form amount of famotidine is applied by spray coating.

D. Over Coating Layer

Opadry II white is applied over the famotidine layer by spray coating.

18.8 Example 8

Manufacture of Ibuprofen/Famotidine Unit Dose Forms

In one version, the oral dosage form comprises many small particles of famotidine coated with a barrier layer and situated in a matrix containing ibuprofen.

A famotidine suspension (75% famotidine, 20% Opadry, 5% talc) is sprayed onto microcrystalline cellulose (Avicel PH 101) to 100% buildup. The particles are coated with a barrier coating comprised of Opadry II White (cat. # Y-22-7719) and then coated with a protective coating comprised of a PEG 6000 and microcrystalline cellulose (1:1).

The famotidine granules are mixed with ibuprofen granules (prepared as described in Table 27, infra) in a proportion that results in an ibuprofen:famotidine (800:26.6) mixture. Colliodal silicon dioxide, croscarmellose, silicified microcrystalline cellulose, and magnesium stearate are added to the ibuprofen-famotidine mixture, and the resulting mixture is compressed into tablets containing 800 mg ibuprofen and 26.6 mg famotidine (calculated weight).

Optionally the tablets can be coated with a protective coating (overcoating layer).

If ibuprofen DC85 (BASF Aktiengesellschaft, Ludwigshafen, Germany) is used colliodal silicon dioxide, croscarmellose, silicified microcrystalline cellulose may be omitted.

18.9 Example 9

Manufacture of Ibuprofen/Famotidine Unit Dose Forms

This example describes manufacture of a tablet containing ibuprofen granules and coated famotidine granules.

A. Ibuprofen Granule

TABLE 27

| Item | Material | % w/w | mg/tablet | Function/Supplier |
|---|---|---|---|---|
| 1. | Ibuprofen 25 USP | 68.96 | 800 | API/BASF |
| 2. | Lactose Monohydrate NF (80M) | 25.86 | 300 | Binder/Kerry Biosci |
| 3. | Colloidal Silicon Dioxide NF (Cab-O-Sil M5P) | 0.52 | 6 | Glidant/Cabot |
| 4. | Croscarmellose Sodium NF Ac-di-Sol | 2.59 | 30 | Disintegrant/FMC |
| 5A. | Hypromellose USP, Methocel E-5 LV Premium (Intragranular in dry mix) | 1.55 | 18 | Binder/Dow |
| 5B | Hypromellose USP, Methocel E-5 LV Premium (Intragranular as solution) | 0.52 | 6 | Binder/Dow |
| 6. | Purified Water USP | — | q.s. | Process aid |
|  | Total weight | 100.0 | 1160 |  |

Items 1-5A are sifted through Quadro Comil 16-mesh and mixed (Blend 1). Item 5B is dissolved in water and slowly added to Blend 1 using a mixer. Additional water is added and mixed. The wet material is dried at 50° C. for 12 h, milled using a 16-mesh screen with appropriate spacer, and dried until the LOD at 50° C. is below 0.5% w/w. Dried granules and extra granular material is transferred to a V-blender and mixed for 3 minutes.

B. Famotidine Granule

TABLE 28

| Item | Material | % w/w | mg/tablet | Function/Supplier |
|---|---|---|---|---|
| STEP-I (Spray Granulation-Top Spray) | | | | |
| 1 | Microcrystalline Cellulose NF (Avicel PH 101) | 45.47 | 35.5 | Inert material/FMC |
| 2 | Famotidine USP | 34.05 | 26.6 | Active/DRL |
| 3 | Opadry II white (Y-22-7719) | 9.09 | 7.1 | Coating/Colorcon |
| 4 | Talc NF | 2.30 | 1.8 | Glidant/Imperial |
| 5 | Purified water USP | N/A | q.s. | Process aid |
| STEP-II (Barrier Coating-Bottom Spray) | | | | |
| 1 | Opadry White (YS-1-7003) | 9.09 | 7.1 | Coating/Colorcon |
| 2 | Purified water USP | N/A | q.s. | Process aid |
|  | Total weight | 100.0 | 78.1 |  |

Set up the Glatt fluid bed processor and add microcrystalline cellulose to Glatt. Disperse famotidine in purified water under mechanical stirring for 5 minutes. Add Opadry followed by talc and let it run for 30 minutes. Homogenize the above suspension for 20-30 minutes. Keep mixing at slow speed to avoid air entrapment Set up the peristaltic pump and spray the drug suspension completely. Dry the product to a product temperature of around 40-44°. Sift the spray granulated famotidine through Quadro comil #20 mesh.

Spray Opadry suspension equivalent to 10% weight gain in the Glatt fluid bed processor. Dry the final product to a product temperature of around 40-44° C. Discharge and sift it through ASTM #30 mesh to remove any agglomerate.

C. Final Blending

TABLE 29

| Item | Material | % w/w | mg/tablet | Function/Supplier |
|---|---|---|---|---|
| 1 | Ibuprofen Granules | 87.34 | 1160.0 | Process Granule |
| 2 | Famotidine Coated Granules | 5.88 | 78.10 | Process Granule |
| 3 | Prosolv SMCC 90 | 3.54 | 47.00 | Diluent/JRS |
| 4 | Croscarmellose Sodium NF | 2.26 | 30.00 | Disintegrant/FMC |
| 5 | Colloidal Silicon Dioxide NF | 0.30 | 4.00 | Glidant/Cabot |
| 6 | Magnesium Stearate NF | 0.68 | 9.00 | Lubricant/Peter Greven |
|  | Total weight | 100.0 | 1328.1 |  |

Weigh appropriate amount of ibuprofen granules, famotidine granules and the extra-granular materials. Blend geometrically famotidine and ibuprofen granules in appropriate blenders.

Add the sifted extra-granular materials (Prosolv SMCC 90, croscarmellose sodium and colloidal silicon dioxide sifted through 16-mesh screen) to above granules and mix for 3 minutes.

Sift magnesium stearate through 30 mesh screen and transfer to the above blender and lubricate for 3 minutes.

D. Tabletting

Set DC-16 compression machine with bisect punches and compress the blend to tablets with target weight of 1.328 g, hardness of 10-20 Kp, disintegration time less than 15 minutes.

E. Film Coating

TABLE 30

| Item | Material | % w/w | mg/tablet | Function/Supplier |
|---|---|---|---|---|
| 1 | Ibuprofen/famotidine Granules |  | 1328.1 | Process Granule/PII |
| 2 | Opadry II White (85F18422) | ~3.0 | 39.90 | Coating/Colorcon |
| 3 | Purified water USP |  | q.s. | Process aid/PII |
|  | Total weight | 100.0 | 1368.0 |  |

Disperse Opadry II white (85 F18422) in water under mechanical stirring. Continue mixing for 45 minutes at slow speed. Load approximately 80-90 kg of compressed tablets in Acella Cota with a 48" coating pan. Coat the tablets to a weight gain of 2.5-3.5% w/w following optimum coating parameters.

In other related embodiments tablets are made as above except that the amount of any non-API component can vary from the amounts above by up to plus or minus 10%. For example, the lactose monohydrate component in Table 27 could vary in the range from about 23.3 to about 28.4. APIs can vary in amounts as described elsewhere herein.

18.10 Example 10

Stability of Ibuprofen/Famotidine Tablet (800/26.6 mg) with Opadry Coatings As described above, a barrier layer separating ibuprofen and famotidine can be comprised of a wide variety of compounds. Many suitable coating material are commercially available as "Opadry" including, for example Opadry II White (Colorcon Code Y-22-7719) which contains HPMC, Glycerol, Polydextrose, Titanium Dioxide, Triacetate, and Macrogol; Opadry white (Colorcon Code YS-1-7003) HPMC 2910, PEG 400, Polysorbate 80, and Titanium Dioxide; and Opadry II White (Colorcon Code 85F18422) which contains PVA-partial hydrolyzed, Titanium Dioxide (E171), Macrogol 3350, and Talc.

Tablets were prepared essentially as described in Example 9 ("Opadry White YS-1-7003") or essentially as described in Example 8 (i.e., as in Example 9 except that Opadry II [Y-22-7719] was used instead of Opadry White in the barrier layer and an additional protective layer was applied by coating with a suspension of PEG 6000 and microcrystalline cellulose [1:1] in water). As shown in Table 31, use of Opadry White in the barrier layer gave superior results compared to Opadry II White.

TABLE 31

EFFECT OF BARRIER COAT ON FAMOTIDINE STABILITY (TOTAL FAMOTIDINE IMPURITIES)

| Time | Opadry II (Y-22-7719) Impurities % | Opadry White (YS-1-7003) Impurities % |
| --- | --- | --- |
| Initial | 0.5 | 0.5 |
| 1 wk 50° C. | 51.0 | 2.0 |
| 2 wk 40° C./75% RH | 3.6 | 0.4 |
| 1 mo 40° C./75% RH | 6.5 | 0.5 |

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

The invention claimed is:

1. An oral dosage in tablet form comprising
a first portion that comprises 800 mg ibuprofen and a second portion that comprises 26.6 mg famotidine,
wherein a barrier layer comprising hydroxyl propyl methyl cellulose 2910, polyoxyethylene glycol 400, polysorbate 80, and titanium dioxide surrounds the second portion completely separating it from the first portion,
wherein upon storage of the oral dosage in tablet form at 40° C. and 75% humidity for one month, no more than about 0.5% total famotidine impurities is present in the oral dosage in tablet form;
wherein the oral dosage in tablet form is formulated so that release of both the ibuprofen and the famotidine occurs rapidly at about the same time,
wherein none of the oral dosage in tablet form, the famotidine, and the ibuprofen is enterically coated or formulated for sustained or delayed release,
wherein the oral dosage in tablet form is for use according to a TID (three times per day) administration schedule for reducing the risk of developing ibuprofen-induced ulcers in a human patient requiring ibuprofen for an ibuprofen-responsive condition selected from the group consisting of rheumatoid arthritis, osteoarthritis, and pain from a condition other than rheumatoid arthritis and osteoarthritis wherein the human patient does not suffer at the times of administering from a condition characterized by hypersecretion of gastric acid and/or from active severe oesophagitis and/or Barrett's ulceration, and/or from gastroesophageal reflux disease.

2. The oral dosage in tablet form of claim 1, wherein the oral dosage in tablet form is packaged with instructions to administer the oral dosage in tablet form according to a TID (three times per day) administration schedule for reducing the risk of developing ibuprofen-induced ulcers in a human patient requiring ibuprofen for an ibuprofen-responsive condition selected from the group consisting of rheumatoid arthritis, osteoarthritis, and pain from a condition other than rheumatoid arthritis and osteoarthritis.

3. The oral dosage in tablet form of claim 1, wherein the oral dosage in tablet form releases at least 60% of the ibuprofen and at least 60% of the famotidine within 20 minutes at a pH of 6.8 to 7.4 under in vitro assay conditions.

4. The oral dosage in tablet form of claim 3, wherein the oral dosage in tablet form releases at least 75% of the ibuprofen and at least 75% of the famotidine within 20 minutes at a pH of 6.8 to 7.4 under in vitro assay conditions.

5. The oral dosage in tablet form of claim 1, wherein the second portion further comprises microcrystalline cellulose.

6. The oral dosage in tablet form of claim 1, wherein the oral dosage in tablet form is prepared by a process comprising:
blending 800 mg ibuprofen with at least one pharmaceutically acceptable excipient to yield the first portion;
blending 26.6 mg famotidine with at least one pharmaceutically acceptable excipient to yield the second portion;
coating said second portion with a barrier layer comprising hydroxyl propyl methyl cellulose 2910, polyoxyethylene glycol 400, polysorbate 80, and titanium dioxide to form a barrier layer-encased second portion;
combining said first portion and said barrier layer-encased coated second portion to yield a combined first and second portion wherein the first and second portions are separated by the barrier layer; and
compressing said combined first and second portion to yield the oral dosage in tablet form.

7. The oral dosage in tablet form of claim 6, wherein the second portion further comprises microcrystalline cellulose.

8. A method for reducing the risk of developing ibuprofen-induced ulcers in a human patient requiring ibuprofen for an ibuprofen-responsive condition selected from the group consisting of rheumatoid arthritis, osteoarthritis, and pain from a condition other than rheumatoid arthritis and osteoarthritis, said human patient being at risk of developing ibuprofen-induced ulcers, said method consisting essentially of:
administering to the human patient a first dose of an oral dosage in tablet form of claim 1,
administering to the human patient a second dose of the oral dosage in tablet form; and
administering to the human patient a third dose of the oral dosage in tablet form, wherein the first, second, and third doses are administered according to a TID (three times per day administration) schedule in a total daily dose of famotidine of about 80 mg, effective for reducing the risk of said human patient developing ibuprofen-induced ulcers, and also for reducing a symptom for which ibuprofen was required, and further wherein the human patient does not suffer at the times of administering from a condition characterized by hypersecretion of gastric acid and/or from active severe oesophagitis and/or Barrett's ulceration, and/or from gastroesophageal reflux disease.

9. The oral dosage in tablet form of claim 1, wherein the only active ingredient for decreasing gastric acid secretion or neutralizing gastric acid in said oral dosage in tablet form is famotidine.

10. An oral dosage in tablet form consisting essentially of:
a first portion that comprises 800 mg ibuprofen and a second portion that comprises 26.6 mg famotidine,
wherein a barrier layer comprising hydroxyl propyl methyl cellulose 2910, polyoxyethylene glycol 400, polysorbate 80, and titanium dioxide surrounds the second portion completely separating it from the first portion, wherein upon storage of the oral dosage in tablet form at 40° C. and 75% humidity for one month, no more than about 0.5% total famotidine impurities is present in the oral dosage in tablet form;

wherein the oral dosage in tablet form is formulated so that release of both the ibuprofen and the famotidine occurs rapidly at about the same time, wherein none of the oral dosage in tablet form, the famotidine, and the ibuprofen is enterically coated or formulated for sustained or delayed release, and wherein the oral dosage in tablet form is for use according to a TID (three times per day) administration schedule for reducing the risk of developing ibuprofen-induced ulcers in a human patient requiring ibuprofen for an ibuprofen-responsive condition selected from the group consisting of rheumatoid arthritis, osteoarthritis, and pain from a condition other than rheumatoid arthritis and osteoarthritis wherein the human patient does not suffer at the times of administering from a condition characterized by hypersecretion of gastric acid and/or from active severe oesophagitis and/or Barrett's ulceration, and/or from gastroesophageal reflux disease.

* * * * *